United States Patent
Chen et al.

(10) Patent No.: US 10,792,492 B2
(45) Date of Patent: Oct. 6, 2020

(54) METHODS, SYSTEMS AND COMPUTER PROGRAM PRODUCTS FOR DETERMINING PHYSIOLOGIC STATUS PARAMETERS USING SIGNALS DERIVED FROM MULTISPECTRAL BLOOD FLOW AND PERFUSION IMAGING

(71) Applicant: East Carolina University, Greenville, NC (US)

(72) Inventors: Cheng Chen, Greenville, NC (US); Thomas Bruce Ferguson, Jr., Raleigh, NC (US); Sunghan Kim, Winterville, NC (US); Zhiyong Peng, Greenville, NC (US); Kenneth Michael Jacobs, Greenville, NC (US)

(73) Assignee: East Carolina University, Greenville, NC (US)

( * ) Notice: Subject to any disclaimer, the term of this patent is extended or adjusted under 35 U.S.C. 154(b) by 0 days.

(21) Appl. No.: 15/518,545

(22) PCT Filed: Oct. 13, 2015

(86) PCT No.: PCT/US2015/055234
§ 371 (c)(1),
(2) Date: Apr. 12, 2017

(87) PCT Pub. No.: WO2016/061041
PCT Pub. Date: Apr. 21, 2016

(65) Prior Publication Data
US 2017/0274205 A1    Sep. 28, 2017

Related U.S. Application Data

(60) Provisional application No. 62/136,010, filed on Mar. 20, 2015, provisional application No. 62/063,663, filed on Oct. 14, 2014.

(51) Int. Cl.
*G06K 9/00* (2006.01)
*A61N 1/08* (2006.01)
(Continued)

(52) U.S. Cl.
CPC .............. *A61N 1/08* (2013.01); *A61B 5/0082* (2013.01); *A61B 5/0261* (2013.01); *A61B 5/05* (2013.01);
(Continued)

(58) Field of Classification Search
CPC ..... A61B 5/05; A61B 5/7207; A61B 2576/02; A61B 5/0082; A61B 5/02405;
(Continued)

(56) References Cited

U.S. PATENT DOCUMENTS

| 4,541,433 A | 9/1985 | Baudino |
| 5,058,596 A | 10/1991 | Makino et al. |

(Continued)

FOREIGN PATENT DOCUMENTS

| CN | 101784227 A | 7/2010 |
| CN | 102083362 A | 6/2011 |

(Continued)

OTHER PUBLICATIONS

Extended European Search Report corresponding to related European Patent Application No. 15850641.0 (9 pages) (dated Apr. 23, 2018).

(Continued)

*Primary Examiner* — Avinash Yentrapati
(74) *Attorney, Agent, or Firm* — Stanek, Lemon, Crouse & Meeks, PA

(57) ABSTRACT

Methods for calculating a MetaKG signal are provided. The method including illuminating a region of interest in a sample with a near-infrared (NIR) light source and/or a visible light source; acquiring images of the region of
(Continued)

interest; processing the acquired images to obtain metadata associated with the acquired images; and calculating the MetaKG signal from the metadata associated with the acquired images. Related systems and computer program products are also provided.

33 Claims, 33 Drawing Sheets

(51) Int. Cl.
    *A61B 5/00*     (2006.01)
    *A61B 5/026*     (2006.01)
    *G16H 50/70*     (2018.01)
    *A61B 5/05*     (2006.01)
    *G06F 19/00*     (2018.01)
    *G06T 7/00*     (2017.01)
    *A61B 5/024*     (2006.01)
    *G06T 5/00*     (2006.01)

(52) U.S. Cl.
    CPC ........ *G06F 19/3481* (2013.01); *G06T 7/0012* (2013.01); *G16H 50/70* (2018.01); *A61B 5/02405* (2013.01); *A61B 5/7207* (2013.01); *A61B 5/7253* (2013.01); *A61B 5/7278* (2013.01); *A61B 2576/02* (2013.01); *G06K 9/00* (2013.01); *G06T 5/00* (2013.01); *G06T 7/00* (2013.01); *G06T 2207/30048* (2013.01)

(58) Field of Classification Search
    CPC ... A61B 5/0261; A61B 5/7253; A61B 5/7271; G06T 7/0012; G06T 2207/30048; G06T 5/00; G06T 7/00; G16H 50/70
    See application file for complete search history.

(56) References Cited

U.S. PATENT DOCUMENTS

| | | | |
|---|---|---|---|
| 5,074,307 A | 12/1991 | Aizu et al. | |
| 5,129,400 A | 7/1992 | Makino et al. | |
| 5,161,531 A | 11/1992 | Parsons et al. | |
| 5,240,006 A | 8/1993 | Fujii et al. | |
| 5,291,885 A | 3/1994 | Taniji et al. | |
| 5,291,886 A | 3/1994 | Katayama et al. | |
| 5,490,505 A | 2/1996 | Diab et al. | |
| 5,588,436 A | 12/1996 | Narayanan et al. | |
| 5,692,510 A | 12/1997 | Gordon et al. | |
| 5,860,922 A | 1/1999 | Gordon et al. | |
| 6,045,511 A | 4/2000 | Ott et al. | |
| 6,263,227 B1 | 7/2001 | Boggett et al. | |
| 6,323,880 B1 | 11/2001 | Yamada | |
| 6,537,223 B1 | 3/2003 | Kristiansen | |
| 6,587,701 B1* | 7/2003 | Stranc | A61B 5/14551 600/310 |
| 6,631,286 B2 | 10/2003 | Pfeiffer et al. | |
| 6,671,540 B1 | 12/2003 | Hochman | |
| 6,766,188 B2 | 7/2004 | Soller | |
| 6,915,154 B1 | 7/2005 | Docherty et al. | |
| 6,944,494 B2 | 9/2005 | Forrester et al. | |
| 6,974,416 B2 | 12/2005 | Booker et al. | |
| 7,031,504 B1* | 4/2006 | Argiro | A61B 6/504 382/131 |
| 7,096,058 B2 | 8/2006 | Miyahara et al. | |
| 7,113,817 B1* | 9/2006 | Winchester, Jr. | A61B 3/1233 356/27 |
| 7,200,431 B2 | 4/2007 | Franco et al. | |
| 7,231,243 B2 | 6/2007 | Tearney et al. | |
| 7,270,637 B2 | 9/2007 | Shin | |
| 7,309,313 B2 | 12/2007 | Nakata et al. | |
| 7,404,640 B2 | 7/2008 | Ferguson et al. | |
| 7,468,039 B2 | 12/2008 | Lui | |
| 7,496,395 B2 | 2/2009 | Serov et al. | |
| 7,541,602 B2 | 6/2009 | Metzger et al. | |
| 7,542,790 B2 | 6/2009 | Jensen et al. | |
| 7,809,225 B2 | 10/2010 | Bouma et al. | |
| 7,809,226 B2 | 10/2010 | Bouma et al. | |
| 9,028,421 B2 | 5/2015 | Fujii et al. | |
| 9,226,673 B2 | 1/2016 | Ferguson, Jr. et al. | |
| 9,271,658 B2 | 3/2016 | Ferguson, Jr. et al. | |
| 9,610,021 B2* | 4/2017 | Dvorsky | A61B 5/0059 |
| 9,640,218 B2* | 5/2017 | Shoemaker | G11B 27/028 |
| 2001/0035503 A1 | 11/2001 | Quistorff et al. | |
| 2002/0016533 A1 | 2/2002 | Marchitto et al. | |
| 2002/0173723 A1 | 11/2002 | Lewis et al. | |
| 2003/0120156 A1* | 6/2003 | Forrester | A61B 5/0261 600/473 |
| 2003/0225328 A1 | 12/2003 | DeMeester et al. | |
| 2003/0231511 A1 | 12/2003 | Thibault | |
| 2004/0068164 A1* | 4/2004 | Diab | A61B 5/14546 600/323 |
| 2005/0046969 A1 | 3/2005 | Beatson et al. | |
| 2006/0058662 A1 | 3/2006 | Kobayashi et al. | |
| 2006/0241460 A1 | 10/2006 | Kimura et al. | |
| 2006/0291708 A1 | 12/2006 | Dehmeshki et al. | |
| 2007/0008615 A1 | 1/2007 | Miyawaki et al. | |
| 2007/0100245 A1 | 5/2007 | Kashima | |
| 2007/0109784 A1 | 5/2007 | Kosnick et al. | |
| 2007/0203413 A1* | 8/2007 | Frangioni | A61B 1/3132 600/478 |
| 2008/0025579 A1* | 1/2008 | Sidlauskas | G06K 9/0004 382/124 |
| 2008/0049268 A1 | 2/2008 | Hardy et al. | |
| 2008/0071176 A1 | 3/2008 | Docherty et al. | |
| 2008/0107361 A1 | 5/2008 | Asukai et al. | |
| 2008/0132794 A1 | 6/2008 | Alfano et al. | |
| 2008/0188726 A1 | 8/2008 | Presura et al. | |
| 2008/0262359 A1 | 10/2008 | Tearney et al. | |
| 2009/0041201 A1 | 2/2009 | Wang et al. | |
| 2009/0054908 A1* | 2/2009 | Zand | A61B 34/30 606/130 |
| 2009/0118623 A1* | 5/2009 | Serov | A61B 5/0059 600/476 |
| 2009/0177098 A1 | 7/2009 | Yakubo et al. | |
| 2009/0209834 A1 | 8/2009 | Fine | |
| 2009/0214098 A1* | 8/2009 | Hornegger | A61B 6/466 382/131 |
| 2009/0216098 A1* | 8/2009 | Stranc | A61B 5/14551 600/328 |
| 2009/0275841 A1* | 11/2009 | Melendez | A61B 5/0059 600/476 |
| 2010/0056936 A1 | 3/2010 | Fujii et al. | |
| 2010/0067767 A1 | 3/2010 | Arakita et al. | |
| 2010/0069759 A1* | 3/2010 | Schuhrke | G06T 5/50 600/476 |
| 2010/0168585 A1* | 7/2010 | Fujii | A61B 5/0261 600/476 |
| 2010/0172567 A1* | 7/2010 | Prokoski | A61B 5/415 382/132 |
| 2010/0209002 A1 | 8/2010 | Thiel et al. | |
| 2010/0284693 A1 | 11/2010 | Agmon et al. | |
| 2010/0305454 A1* | 12/2010 | Dvorsky | A61B 5/0059 600/476 |
| 2011/0013002 A1* | 1/2011 | Thompson | A61B 5/0261 348/77 |
| 2011/0068007 A1 | 3/2011 | Pang et al. | |
| 2011/0071382 A1 | 3/2011 | Miyazaki et al. | |
| 2011/0137169 A1 | 6/2011 | Akaki et al. | |
| 2011/0164035 A1* | 7/2011 | Liao | A61B 6/4266 345/419 |
| 2011/0169978 A1 | 7/2011 | Lasser et al. | |
| 2011/0176048 A1 | 7/2011 | Rockley | |
| 2011/0319775 A1 | 12/2011 | Fujii et al. | |
| 2012/0071769 A1 | 3/2012 | Dunn et al. | |
| 2012/0078113 A1 | 3/2012 | Hitestone et al. | |
| 2012/0095354 A1 | 4/2012 | Dunn et al. | |
| 2012/0108956 A1 | 5/2012 | Warger, II et al. | |
| 2012/0165627 A1* | 6/2012 | Yamamoto | A61B 1/0653 600/317 |
| 2012/0191005 A1 | 7/2012 | Sobol et al. | |
| 2012/0277559 A1* | 11/2012 | Kohl-Bareis | A61B 5/0261 600/324 |

(56) References Cited

U.S. PATENT DOCUMENTS

| | | | | |
|---|---|---|---|---|
| 2013/0204112 A1* | 8/2013 | White | ............... | A61B 5/6826 600/407 |
| 2013/0223705 A1* | 8/2013 | Ferguson, Jr. | ........ | G06T 7/0012 382/128 |
| 2013/0245456 A1* | 9/2013 | Ferguson, Jr. | ....... | A61B 5/0044 600/473 |
| 2013/0324866 A1* | 12/2013 | Gladshtein | ........... | A61B 5/0295 600/507 |
| 2013/0345560 A1* | 12/2013 | Ferguson, Jr. | ....... | A61B 5/0275 600/431 |
| 2014/0003740 A1 | 1/2014 | Bone | | |
| 2014/0081133 A1* | 3/2014 | Nie | ......................... | A61B 5/06 600/431 |
| 2014/0161421 A1* | 6/2014 | Shoemaker | ........... | G06T 7/0016 386/278 |
| 2014/0187966 A1 | 7/2014 | Theirman | | |
| 2014/0213861 A1 | 7/2014 | Van Leest | | |
| 2014/0276097 A1 | 9/2014 | Sharonov | | |
| 2014/0285702 A1 | 9/2014 | Higashiyama et al. | | |
| 2014/0293091 A1* | 10/2014 | Rhoads | ................ | G01J 3/2823 348/234 |
| 2014/0340482 A1 | 11/2014 | Kanarowski | | |
| 2015/0077716 A1 | 3/2015 | Peng | | |
| 2015/0148623 A1* | 5/2015 | Benaron | .............. | A61B 5/4875 600/306 |
| 2015/0196257 A1* | 7/2015 | Yousefi | ................. | A61B 5/024 600/324 |
| 2015/0342479 A1* | 12/2015 | Liu | .................... | A61B 5/02416 600/479 |
| 2016/0198961 A1* | 7/2016 | Homyk | ................ | A61B 5/0082 600/476 |
| 2016/0270672 A1* | 9/2016 | Chen | .................... | A61B 5/0077 |
| 2016/0278718 A1* | 9/2016 | Fujii | ..................... | A61B 5/7282 |
| 2016/0317041 A1* | 11/2016 | Porges | ................. | A61B 5/0037 |
| 2016/0358332 A1* | 12/2016 | Watanabe | .............. | G06T 7/0012 |
| 2017/0017858 A1* | 1/2017 | Roh | ........................ | G02B 27/48 |
| 2017/0049377 A1* | 2/2017 | Littell | .................... | A61B 5/032 |
| 2017/0059408 A1* | 3/2017 | Korner | .............. | G01B 11/2509 |
| 2017/0091962 A1* | 3/2017 | Hagiwara | ............ | G06T 11/008 |
| 2017/0135555 A1* | 5/2017 | Yoshizaki | ............ | A61B 1/0002 |
| 2017/0224274 A1 | 8/2017 | Chen et al. | | |
| 2017/0270379 A1* | 9/2017 | Kasai | .................... | G06K 9/6215 |
| 2018/0153422 A1* | 6/2018 | Watanabe | .......... | A61B 5/02433 |

FOREIGN PATENT DOCUMENTS

| | | |
|---|---|---|
| CN | 102770071 A | 11/2012 |
| CN | 103340601 A | 10/2013 |
| CN | 103417196 A | 12/2013 |
| EP | 2 524 650 A2 | 11/2012 |
| JP | 10-290791 | 11/1998 |
| JP | 2005-118325 | 5/2005 |
| JP | 2005-185834 | 7/2005 |
| JP | 2007-125144 A | 5/2007 |
| JP | 2008-139543 | 6/2008 |
| JP | 2011-249267 A | 12/2011 |
| JP | 2012-130629 | 7/2012 |
| JP | 2013-118978 A | 6/2013 |
| JP | 2014-000246 A | 1/2014 |
| JP | 2015-223463 | 12/2015 |
| WO | WO 96/12435 | 5/1996 |
| WO | 97/43950 | 11/1997 |
| WO | 98/44839 | 10/1998 |
| WO | WO 2006/021096 A1 | 3/2006 |
| WO | WO 2006/116672 A2 | 11/2006 |
| WO | WO 2009/127972 A2 | 10/2009 |
| WO | WO 2010/131550 A1 | 11/2010 |
| WO | WO 2012/096878 A2 | 7/2012 |
| WO | WO 2013/190391 A2 | 12/2013 |
| WO | WO 2014/006465 A1 | 1/2014 |
| WO | WO 2014/009859 A2 | 1/2014 |
| WO | WO 2016/153741 A1 | 9/2016 |

OTHER PUBLICATIONS

First Office Action, Chinese Patent Application No. 201580066744. 6, dated Oct. 9. 2019, 23 pages.

Gioux et al., "Motion-gated acquisition for in vivo optical imagmg," Journal of Biomedical Optics, Nov./Dec. 2009, vol. 14(6), pp. 064038-1 through 084038-8.

U.S. Appl. No. 15/054,830, Chen et al., filed Feb. 26, 2016.

U.S. Appl. No. 15/559,605, Peng et al., filed Sep. 19, 2017.

U.S. Appl. No. 15/559,646, Peng et al., filed Sep. 19, 2017.

Nakamura et al., "Applying Hyper Eye Medical System; HEMS to abdominal surgery," Progress in Medicine, Mar. 10, 2011, vol. 31. No. 3, 806-809.

Notification of Reason(s) for Refusal, JP 2017-519923. dated Mar. 10, 2020, 7 pages.

Notification of Reason(s) for Refusal, JP 2017-568002, dated Mar. 31, 2020, 6 pages.

U.S. Appl. No. 15/688,472, Chen et al., filed Aug. 28, 2017.

Furstenberg et al. "Laser speckle reduction techniques for mid-infrared microscopy and stand-off spectroscopy" *Proceedings of SPIE* 10210:1021004-1-8 (2017).

Redding et al. "Speckle-free laser imaging using random laser illumination" *Nature Photonics* 6:355-359 (2012).

Ren et al. "A simultaneous multimodal imaging system for tissue functional parameters" *Proceedings of SPIE* 8937:893706-1-12 (2014).

Zhang et al. "Multimodal imaging of ischemic wounds" *Proceedings of SPIE* 8553:85531G-1-8 (2012).

Gioux et al., "Motion-gated acquisition for in vivo optical imaging," Journal of Biomedical Optics, Nov./Dec. 2009, vol. 14(6), pp. 064038-1 through 064038-8.

Decision of Refusal, Japanese Patent Application No. 2017-519928, dated Jan. 7, 2020, 5 pages.

International Search Report and the Written Opinion of the International Searching Authority corresponding to International Patent Application No. PCT/US2015/055234 (13 pages) (dated Jan. 26, 2016).

Aizu, Y et al. (1991) "Bio-Speckle Phenomena and Their Application to the Evaluation of Blood Flow" Optics and Laser Technology, vol. 23, No. 4, Aug. 1, 1991.

Brezinski, M. E., G. J. Tearney, et al. (1996). "Imaging of coronary artery microstructure (in vitro) with optical coherence tomography." American Journal of Cardiology 77 (1): 92-93.

Briers et al., (1995) "Quasi real-time digital version of single-exposure speckle photography for full-field monitoring of velocity or flow fields," Optics Communications 116: 36-42.

Briers, J. David, (2001) "Laser Doppler, speckle and related techniques for blood perfusion mapping and imaging," Physiol. Meas. 22: R35-R66.

Chen, Z. P., T. E. Milner, et al. (1997). "Noninvasive imaging of in vivo blood flow velocity using optical Doppler tomography." Optics Letters 22(14): 1119-1121.

Cheng et al., (2004) "Laser speckle imaging of blood flow in microcirculation," Phys. Med. Biol., 49: 1347-1357.

Choi et al., "Linear response range characterization and in vivo application of laser speckle imaging of blood flow dynamics," Journal of Biomedical Optics, Jul./Aug. 2006, 11(4): 041129.

Cioffi, G. A. (2001). "Three common assumptions about ocular blood flow and glaucoma." Survey of Ophthalmology 45: S325-S331.

Draijer, Matthijs J., "High Speed Perfusion Imaging Based on Laser Speckle Fluctuations," Printed by Ridderprint, Ridderkerk, The Netherlands 2010, 145 pages.

Draijer et al., "Twente Optical Perfusion Camera: system overview and performance for video rate laser Doppler perfusion imaging," Optics Express, Mar. 2, 2009, 17(5): 3211-3225.

Duncan et al., "Can laser speckle flowmetry be made a quantitative tool?," J. Opt. Soc. Am. A, Aug. 2008, 24(8): 2088-2094.

Dunn et al. "Dynamic imaging of cerebral blood flow using laser speckle", J. of Cerebral Blood Flow and Metabolism 21, 195-201 (2001).

Dunn et al., (2011) A Transmissive Laser Speckle Imaging Technique for Measuring Deep Tissue Blood Flow: An Example Appli-

(56) References Cited

OTHER PUBLICATIONS cation in Finger Joints, Lasers in Surgery and Medicine, 43: 21-28.
Eun, H. C. (1995). "Evaluation of skin blood flow by laser Doppler flowmetry. [Review] [151 refs]." Clinics in Dermatology 13(4): 337-47.
Fercher et al., "Flow Visualization by Means of Single-Exposure Speckle Photography," Optics Communications, Jun. 1, 1981, 37(5): 326-330.
Gandjbakhche, A. H., P. Mills, et al. (1994). "Light-Scattering Technique for the Study of Orientation and Deformation of Red-Blood-Cells in a Concentrated Suspension." Applied Optics 33(6): 1070-1078.
Izatt, J. A., M. D. Kulkarni, et al. (1996). "Optical coherence tomography and microscopy in gastrointestinal tissues." IEEE Journal of Selected Topics in Quantum Electronics 2(4): 1017.
Jang, I. K., G. J. Tearney, et al. (2001). "Visualization of Tissue Prolapse Between Coronary Stent Struts by Optical Coherence Tomography: Comparison With Intravascular Ultrasound." Images in Cardiovascular Medicine, American Heart Association, http://circ.ahajournals.org/content, p. 2754.
Konishi and Fujii "Real-time visualization of retinal microcirculation by laser flowgraphy", Opt. Eng. 34, 753-757 (1995).
Kruijt et al., (2006), "Laser speckle imaging of dynamic changes in flow during photodynamic therapy," Lasers Med Sci, 21: 208-212.
Leitgeb, R. A., L. Schmetterer, et al. (2003). "Real-time assessment of retinal blood flow with ultrafast acquisition by color Doppler Fourier domain optical coherence tomography." Optics Express 11(23): 3116-3121.
Lesnick et al., "New Generation Optical Would Monitoring Device," CW Optics, Inc., Yorktown, Virginia, USA, Admitted Prior Art, 1 page.
Li et al., "Imaging cerebral blood flow through the intact rate skull with temporal laser speckle imaging," Optics Letters, Jun. 15, 2006, 31(12): 1824-1826.
Matsievskii, D.D., (2004) "Blood Flow Measurements in Studies of Macro- and Microcirculation," Bulletin of Experimental Biology and Medicine, 6: 541-544.
Nadkarni, Seemantini K. et al (2005) "Characterization of Atherosclerotic Plaques by Laser Speckle Imaging" Circulation vol. 112, pp. 885-892.
Nelson, J. S., K. M. Kelly, et al. (2001). "Imaging blood flow in human port-wine stain in situ and in real time using optical Doppler tomography." Archives of Dermatology 137(6): 741-744.
Ohtsubo et al., (1976) "Velocity measurement of a diffuse object by using time-varying speckles," Optical and Quantum Electronics, 8: 523-529.
Oshima, M., R. Torii, et al. (2001). "Finite element simulation of blood flow in the cerebral artery." Computer Methods in Applied Mechanics and Engineering 191 (6-7): 661-671.
Parthasarathy et al., "Laser speckle contrast imaging of cerebral blood flow in humans during neurosurgery: a pilot clinical study," Journal of Biomedical Optics, 15(6) Nov./Dec. 2010, pp. 066030-1 to 066030-8.
Rege et al., "Multiexposure laser speckle contrast imaging of the angiogenic microenvironment," Journal of Biomedical Optics, 16(5), May 2011, pp. 056006-1 to 056006-10.

Ren, Hongwu et al., "Phase-Resolved Functional Optical Coherence Tomography: Simultaneous Imaging of In Situ Tissue Structure, Blood Flow Velocity, Standard Deviation, Birefringence, and Stokes Vectors in Human Skin," Optics Letters, vol. 27, No. 19, Oct. 1, 2002, pp. 1702-1704.
Richards G.J. et al. (1997) "Laser Speckle Contrast Analysis (LASCA): A Technique for Measuring Capillary Blood Flow Using the First Order Statistics of Laser Speckle Patterns" Apr. 2, 1997.
Ruth, B. "blood flow determination by the laser speckle method", Int J Microcirc: Clin Exp, 1990, 9:21-45.
Ruth, et al., (1993) "Noncontact Determination of Skin Blood Flow Using the Laser Speckle Method: Application to Patients with Peripheral Arterial Occlusive Disease (PAOD) and to Type-I Diabetes," Lasers in Surgery and Medicine 13: 179-188.
Subhash, Hrebesh M., "Biophotonics Modalities for High-Resolution Imaging of Microcirculatory Tissue Beds Using Endogenous Contrast: A Review of Present Scenario and Prospects," International Journal of Optics, vol. 2011, Article ID 293684, 20 pages.
Tearney et al., "Atherosclerotic plaque characterization by spatial and temporal speckle pattern analysis", CLEO 2001, vol. 56, pp. 307-307.
Wang, X. J., T. E. Milner, et al. (1997). "Measurement of fluid-flow-velocity profile in turbid media by the use of optical Doppler tomography." Applied Optics 36(1): 144-149.
Wardell et al., "ECG-Triggering of the Laser Doppler Perfusion Imaging Signal," Proceedings of the 20$^{th}$ Annual International Conference of the IEEE Engineering in Medicine and Biology Sociсity, vol. 20, No. 4, 1998, pp. 1879-1880.
Weber et al., (2004) "Optical imaging of the spatiotemporal dynamics of cerebral blood flow and oxidative metabolism in the rat barrel cortex," European Journal of Neuroscience, 20: 2664-2670.
White, Brian R. et al., "In Vivo Dynamic Human Retinal Blood Flow Imaging Using Ultra-High-Speed Spectral Domain Optical Doppler Tomography," Optics Express, Dec. 15, 2003, 11(25): 3490-3497.
Wussling et al., "Laser diffraction and speckling studies in skeletal and heart muscle", Biomed, Biochem, Acta, 1986, 45(112):S 23-S 27.
Yazdanfar et al., "In Vivo imaging in blood flow in human retinal vessels using color Doppler optical coherence tomography", SPIE, 1999 vol. 3598, pp. 177-184.
Yazdanfar, S., A. M. Rollins, et al. (2000). "Imaging and velocimetry of human retinal circulation with color Doppler optical coherence tomography." Optics Letters, vol. 25, No. 19, Oct. 1, 2000, pp. 1448-1450.
Yazdanfar, S., A. M. Rollins, et al. (2003). "In vivo imaging of human retinal flow dynamics by color Doppler optical coherence tomography." Archives of Ophthalmology 121(2): 235-239.
Zakharov et al., "Dynamic laser speckle imaging of cerebral blood flow," Optics Express, vol. 17, No. 16, Aug. 3, 2009, pp. 13904-13917.
Zakharov et al., "Quantitative modeling of laser speckle imaging," Optics Letters, Dec. 1, 2006; 31(23): 3465-3467.
Zhao, Y. H., Z. P. Chen, et al. (2000). "Doppler standard deviation imaging for clinical monitoring of in vivo human skin blood flow." Optics Letters 25(18): 1358-1360.

\* cited by examiner

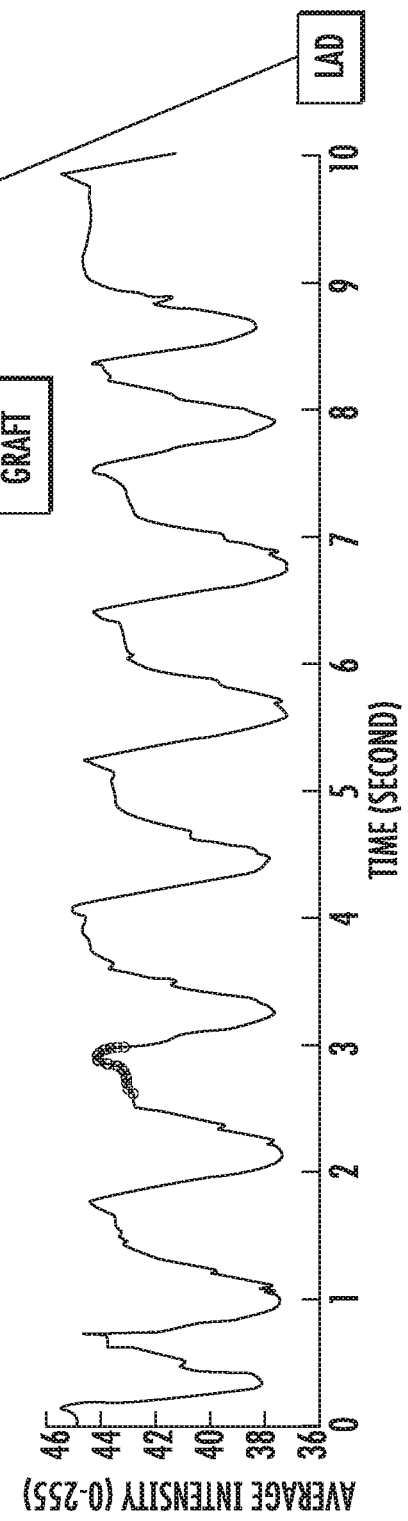

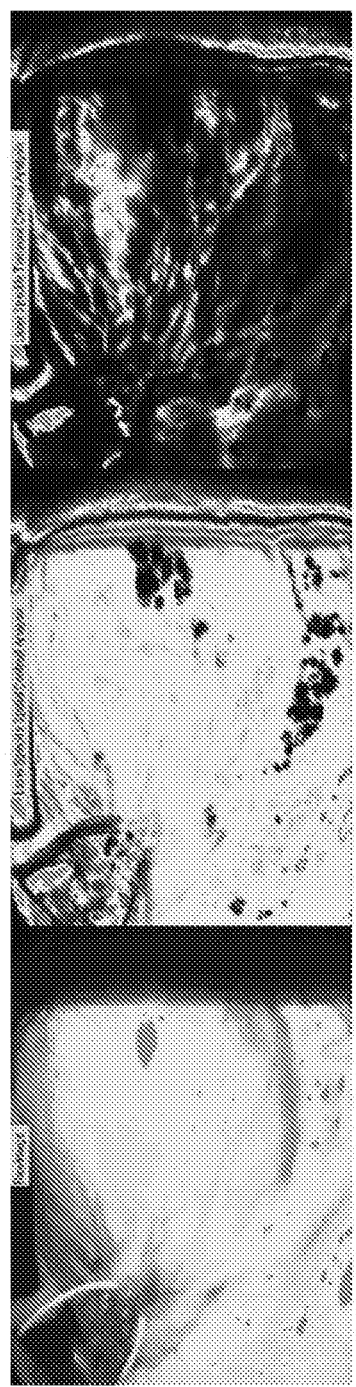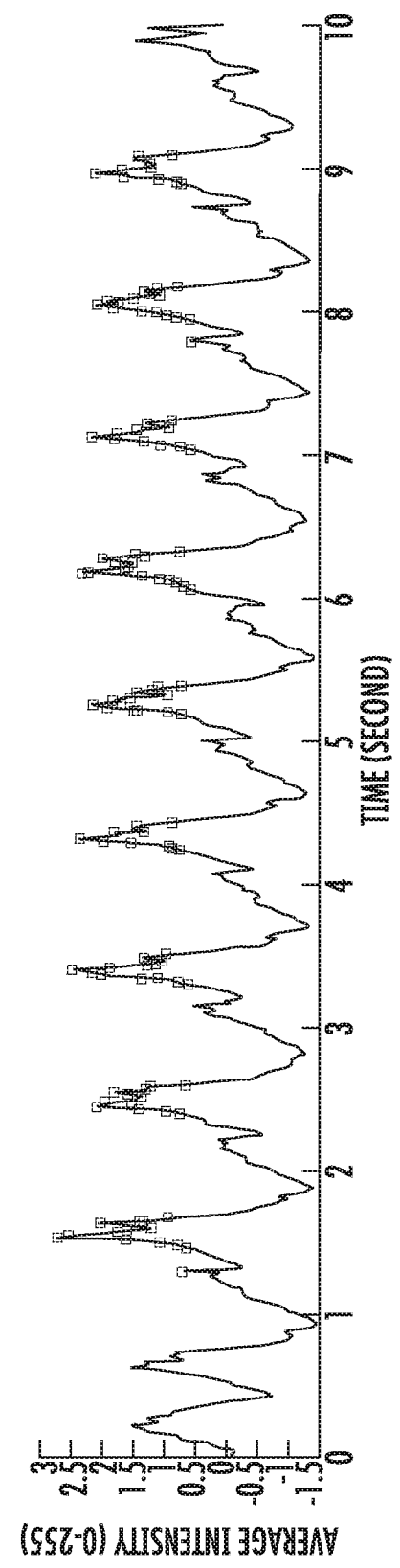
FIG. 6A  FIG. 6B  FIG. 6C
FIG. 7

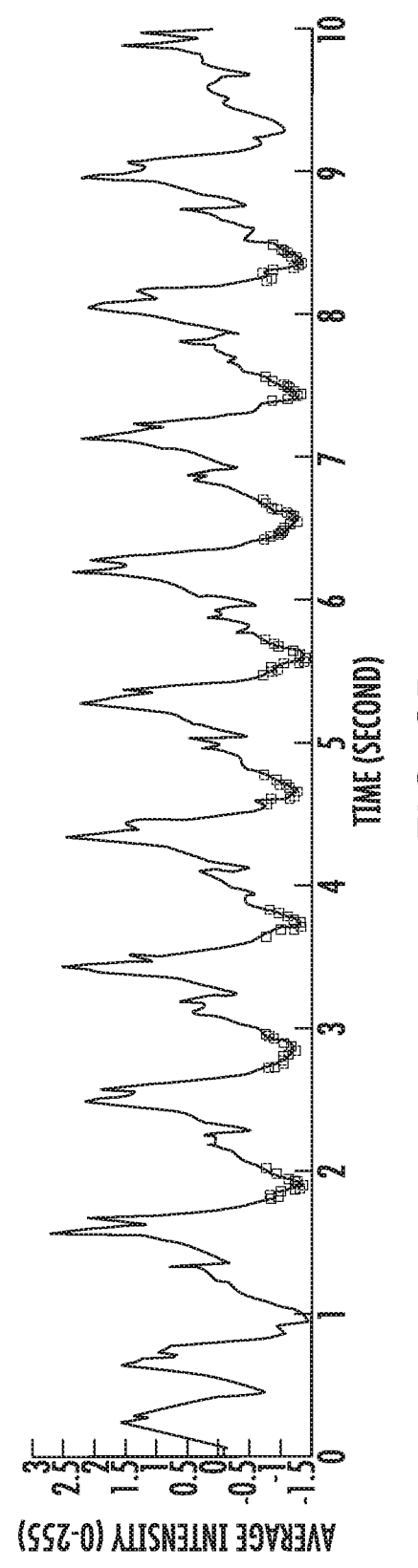
FIG. 8A  FIG. 8B  FIG. 8C
FIG. 8D

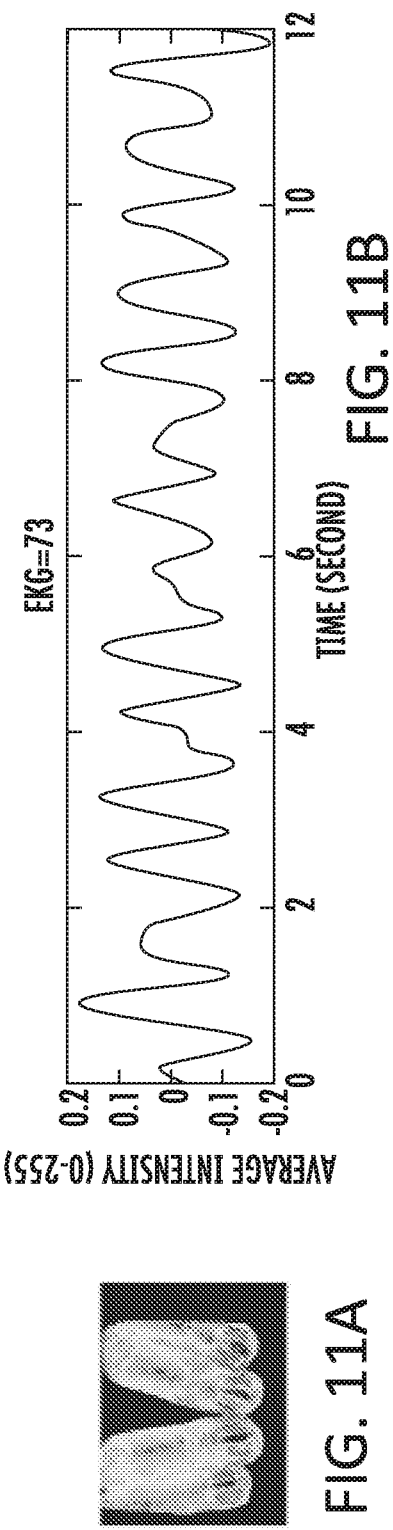
FIG. 11A
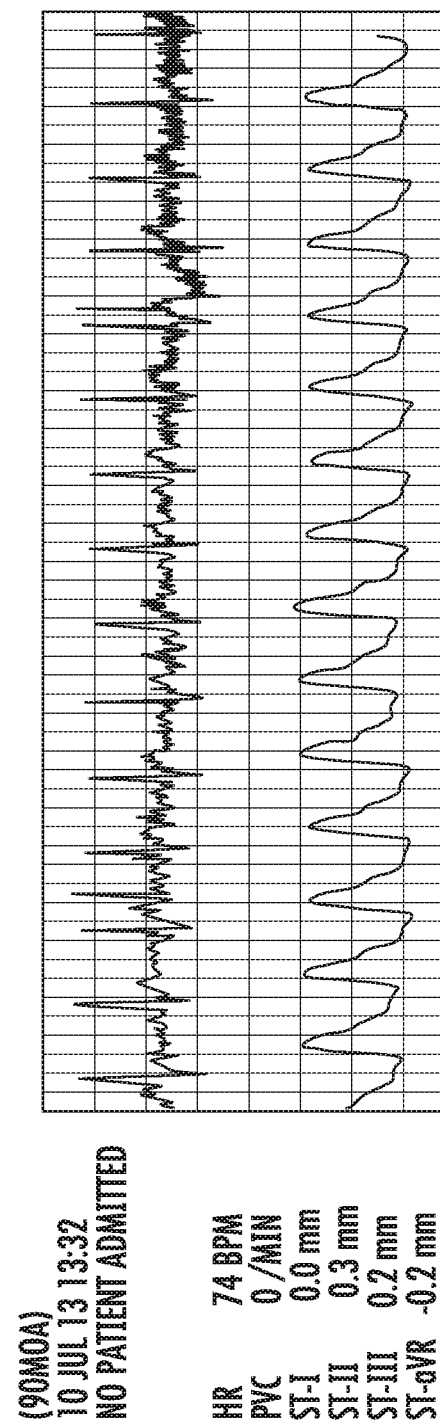
FIG. 11B
FIG. 11C

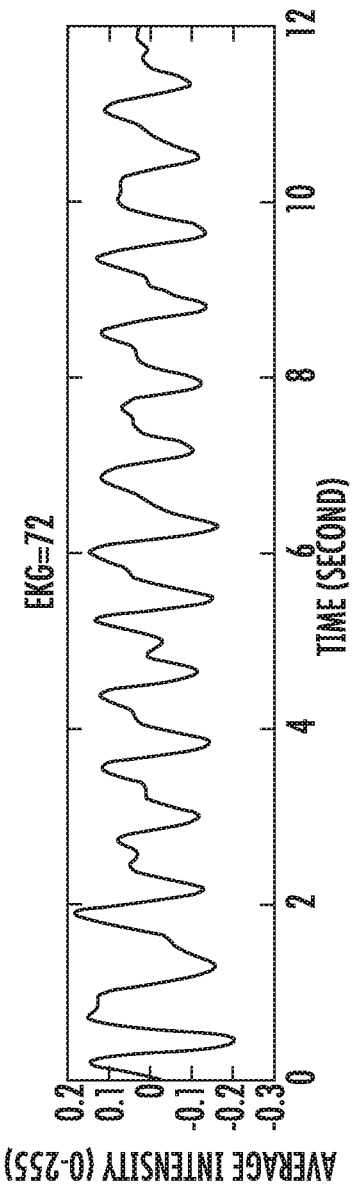
FIG. 15A
FIG. 15B
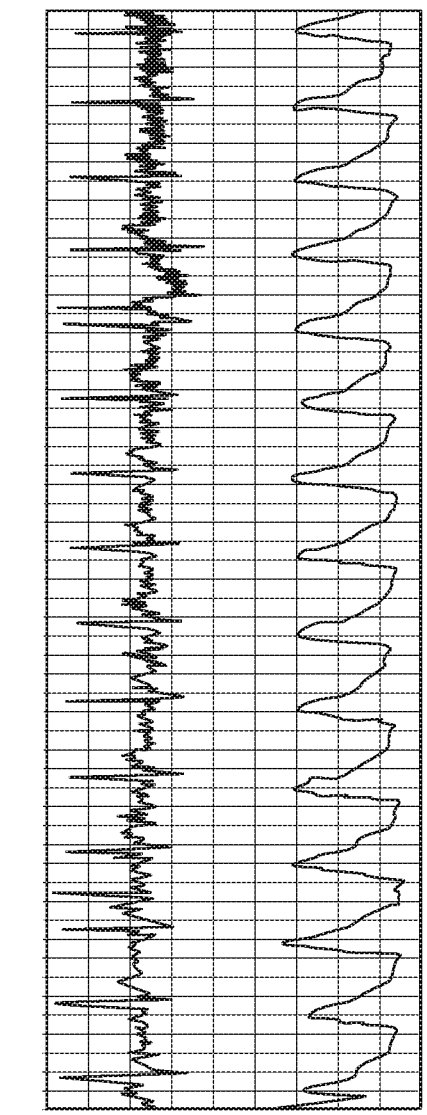
FIG. 15C

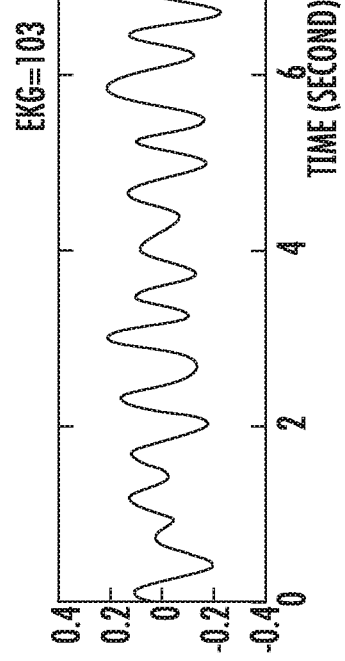
FIG. 17A
FIG. 17B
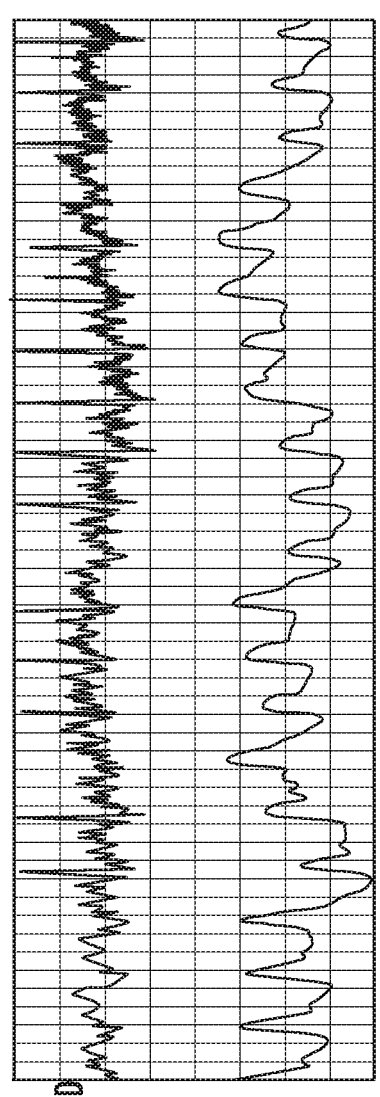
FIG. 17C

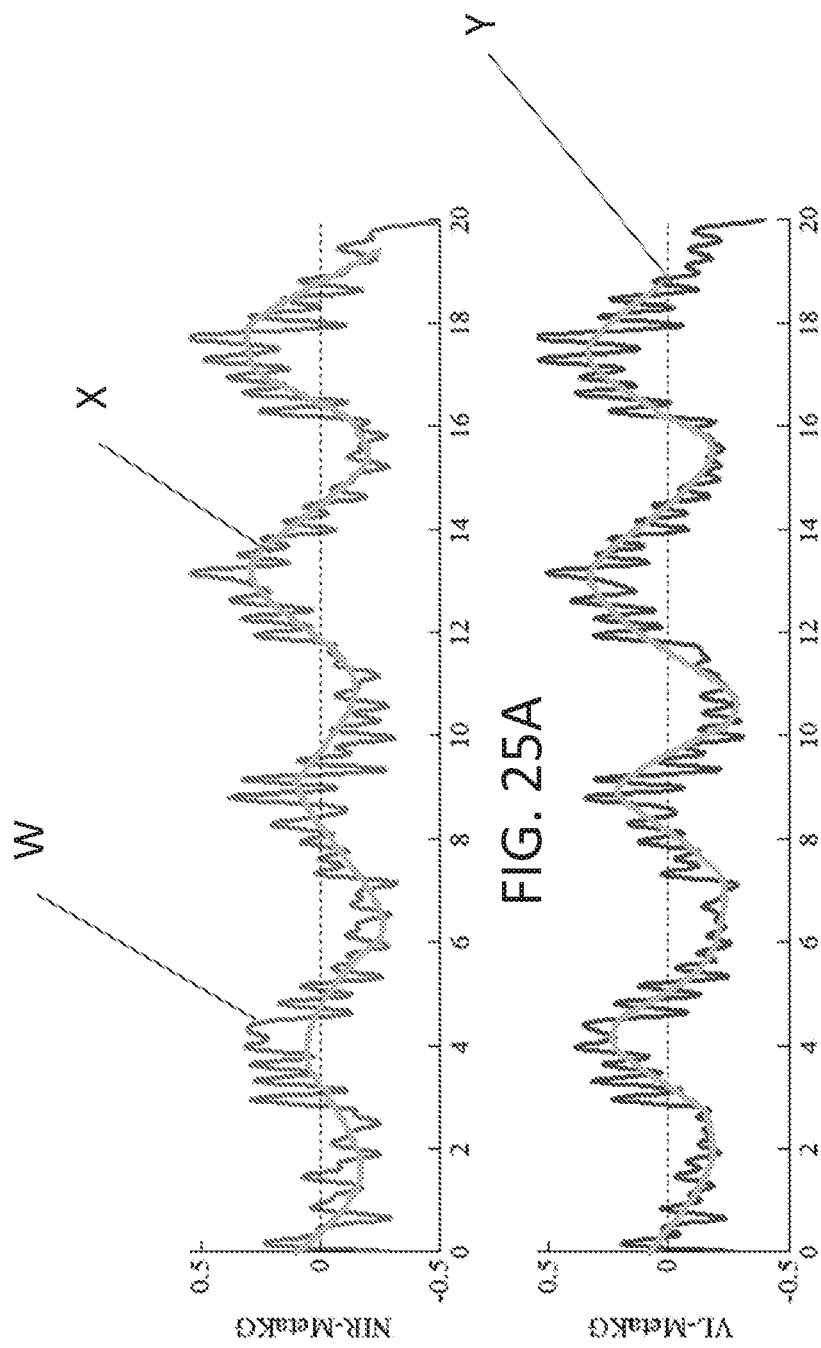

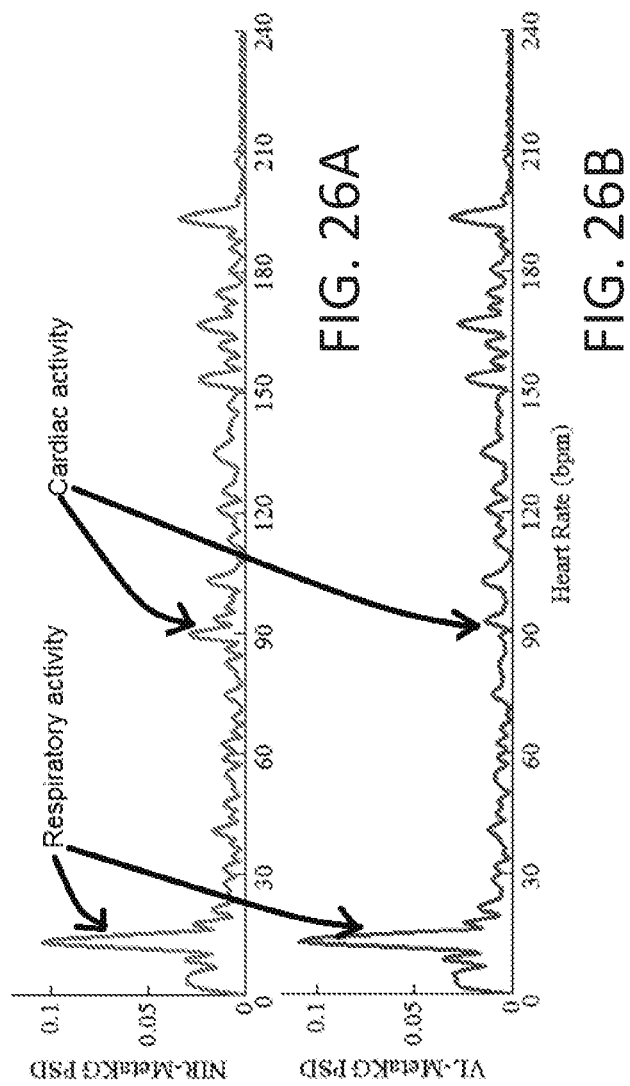

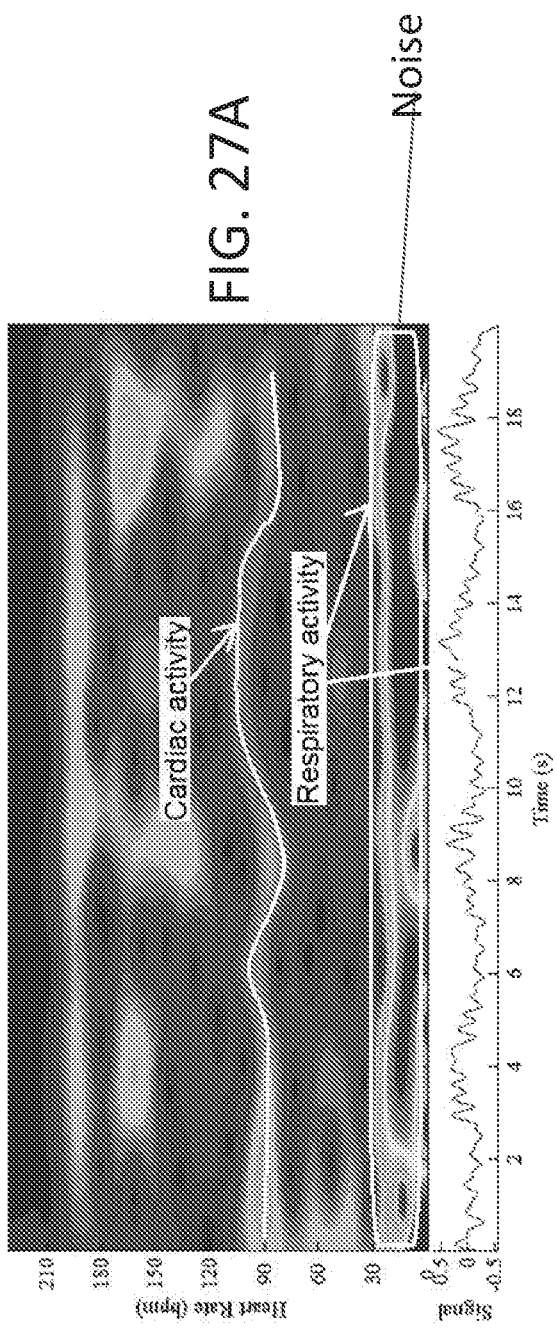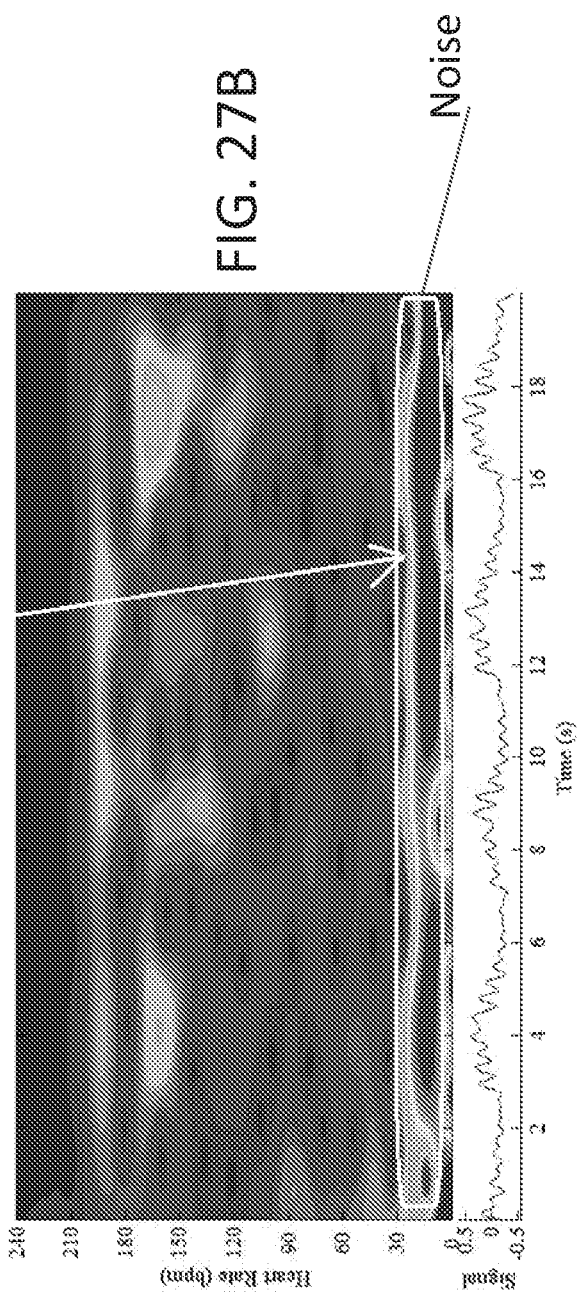

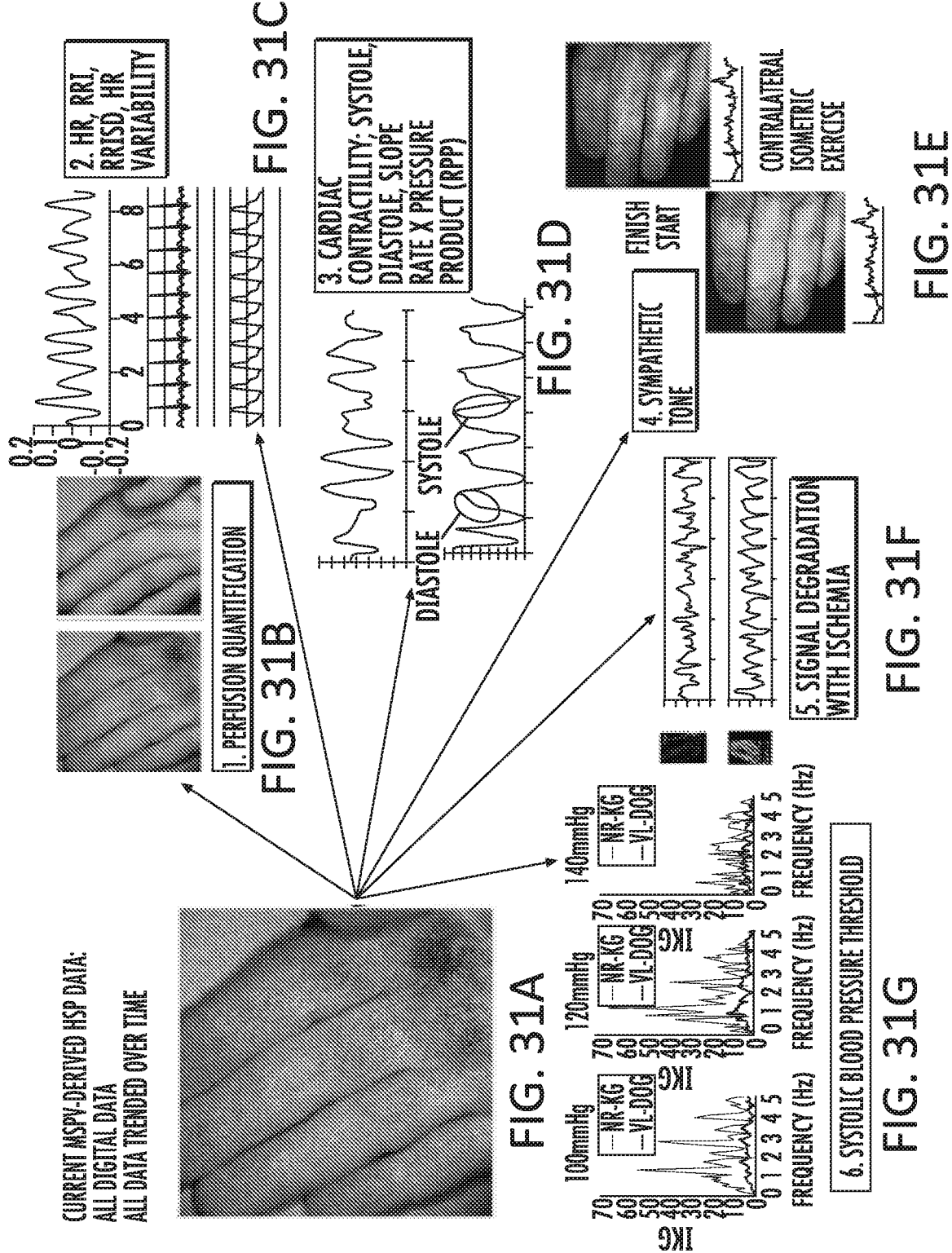

METHODS, SYSTEMS AND COMPUTER PROGRAM PRODUCTS FOR DETERMINING PHYSIOLOGIC STATUS PARAMETERS USING SIGNALS DERIVED FROM MULTISPECTRAL BLOOD FLOW AND PERFUSION IMAGING

CLAIM OF PRIORITY

The present application claims priority from U.S. Provisional Application Nos. 62/063,663, filed Oct. 14, 2014 and 62/136,010, filed Mar. 20, 2015, the disclosures of which are hereby incorporated herein by reference as if set forth in their entirety.

RESERVATION OF COPYRIGHT

A portion of the disclosure of this patent document contains material which is subject to copyright protection. The copyright owner, East Carolina University of Greenville, N.C., has no objection to the reproduction by anyone of the patent document or the patent disclosure, as it appears in the Patent and Trademark Office patent file or records, but otherwise reserves all copyright rights whatsoever.

FIELD

The inventive concept relates generally to visualization of organs and/or tissue and, more particularly, to determining blood flow and perfusion parameters in a sample.

BACKGROUND

Blood flow and perfusion in tissue/organs are defined by the amount of blood transferred per unit time over a 2-dimensional area or in a 3-dimensional structure. Blood flow generally relates to volume of flow/unit time in conduits larger than the arteriolar level (macrovascular level). Perfusion typically refers to the blood flow in the microvascular level, with no current parameters for quantification with non-invasive technologies. Direct measurement and quantification of blood flow and perfusion in real time is still being developed.

Currently, there are several imaging technologies that may be used to measure the magnitude and distribution of fluid velocity, such as Laser Doppler Imaging (LDI) and Laser Speckle Imaging (LSI). Fluid velocity is linear flow demonstrating the direction and magnitude of flow, but does not directly quantify flow in either the microvascular or macrovascular levels. To be linked with the more clinically intuitive concepts and terms of blood flow and perfusion, further assumptions or analysis may be required. Indeed, combined with proper fluid dynamic modeling, these imaging techniques of fluid velocity measurement have the potential to derive quantification information of blood flow and perfusion, in both experimental and human clinical conditions. Throughout this document, the terms "blood flow" and "perfusion" are used instead of the more technically oriented term "fluid velocity."

Blood flow is not a constant in the cardiovascular system in mammalian species. Experimental and clinical data document that there are blood velocity changes within one cardiac cycle because the cardiac output and aortic pressure are not constant within one cardiac cycle. Using the blood flow in coronary arteries as an example, in the systolic phase of the cycle the coronary blood flow is low or even stops due to the contraction of the ventricular myocardium. However, in the diastolic phase the blood flow is comparatively high and reaches a maximum level. Based on specific anatomic and physiologic characteristics, the blood flow and perfusion in other tissues and organs may vary as well influenced by the cardiac cycle, but these different organ systems also have specific conditions of blood flow and perfusion seemingly unrelated to the cardiac cycle. Current techniques to assess blood flow and perfusion cannot make this differentiation in these tissues and organ systems and, therefore, improved techniques may be desired.

SUMMARY

Some embodiments of the present inventive concept provide methods for calculating a MetaKG signal. The method includes illuminating a region of interest in a sample with at least one light source, wherein the light source is a near-infrared (NIR) light source and/or a visible light source; acquiring images of the region of interest; processing the acquired images to obtain metadata associated with the acquired images; and calculating the MetaKG signal from the metadata associated with the acquired images.

In further embodiments, the MetaKG signal may be derived from raw images or from perfusion images.

In still further embodiments, the method may further include acquiring blood flow and perfusion data using the calculated MetaKG signal. Calculating the MetaKG signal may further include generating the MetaKG signal from the acquired images by processing the acquired images to obtain contrast images and calculating average contrast intensity of the contrast images versus time in the region of interest. The method may further include calculating at least one of heart rate and pulsatility information from the average intensity versus time in the region of interest by analyzing a frequency component of the average intensity versus time. The method may further include differentiating between abnormal and normal tissue based on frequency component of the average intensity versus time; and indicating a degree of abnormality related to an underlying physiological response.

In some embodiments, the method may further include extracting heart rate variability (HRV) information from the heart rate calculated from the average contrast intensity versus time in the region of interest.

In further embodiments, the method may further include changing configuration of the region of interest; and generating a two dimensional heart rate map of a region of interest in a field of view. Changing the configuration of the region of interest may include changing at least one of the size and the location of the region of interest.

In still further embodiments, the sample may be one of tissue and an organ.

In some embodiments, calculating the MetaKG signal may include calculating the MetaKG signal using average intensity of speckle contrast images.

In further embodiments, at least one Hemodynamic Status Parameter (HSP) may be determined including Heart Rate (HR); heart rate variability (HRV); R-to-R interval (RRI); RRI Standard Deviation (RRISD); systolic Blood Pressure threshold (SBt); rate×pressure product (RPP); instantaneous perfusion in systole and diastole; frequency analysis and time-frequency analysis of a perfusion curve; and contractility index including slope of the perfusion curve based on the calculated MetaKG.

In still further embodiments, at least one Hemodynamic Status Parameter may be determined including tissue oxygen content, hemoglobin content, and temperature based on the calculated MetaKG signal.

Some embodiments of the present inventive concept provide computer systems for calculating a MetaKG signal. The systems include a processor; and a memory coupled to the processor and comprising computer readable program code that when executed by the processor causes the processor to perform operations including illuminating a region of interest in a sample with at least one light source, wherein the light source is a near-infrared (NIR) light source and/or a visible light source; acquiring images of the region of interest; processing the acquired images to obtain metadata associated with the acquired images; and calculating the MetaKG signal from the metadata associated with the acquired images.

Further embodiments of the present inventive concept provide computer program products for calculating a MetaKG signal. The computer program products including a non-transitory computer readable storage medium having computer readable program code embodied in the medium, the computer readable program code including computer readable program code to illuminate a region of interest in a sample with at least one light source, wherein the light source is a near-infrared (NIR) light source and/or a visible light source; computer readable program code to acquire images of the region of interest; computer readable program code to process the acquired images to obtain metadata associated with the acquired images; and computer readable program code to calculate the MetaKG signal from the metadata associated with the acquired images.

Still further embodiments of the present inventive concept provide methods of removing movement-related artifacts from a MetaKG signal using dual wavelength light sources. The methods include illuminating a region of interest in a sample with a near-infrared (NIR) light source and a visible light (VL) source; acquiring two sets of images of the region of interest each corresponding to one of the NIR light source and the VL source; processing the two sets of images to obtain NIR-metadata and VL-metadata; calculating a NIR MetaKG and a VL MetaKG from the NIR-metadata and the VL metadata, respectively; extracting a movement-related common signal component from the NIR MetaKG and the VL MetaKG; and calculating a noise-free MetaKG by cancelling out the movement-related common signal component from the NIR MetaKG.

In some embodiments, calculating the noise-free MetaKG may include removing noise due to a motion artifact, where the noise due to the motion artifact includes respiratory activity.

BRIEF DESCRIPTION OF THE DRAWINGS

FIGS. 4A through 4C are a series of Laser Speckle images of the heart.

FIG. 5 is a graph illustrating average intensity v. time representing the metaKG signal in accordance with embodiments of the present inventive concept.

FIGS. 6A-C is a series of Laser Speckle images of the heart during a systolic phase.

FIG. 7 is a graph illustrating average intensity v. time representing the metaKG signal in accordance with embodiments of the present inventive concept.

FIGS. 8A-C is a series of Laser Speckle images of the heart during diastolic phase.

FIG. 8D is a graph illustrating average intensity v. time representing the metaKG signal in accordance with embodiments of the present inventive concept.

FIG. 11A is an image illustrating LSI-analyzed velocity map of perfusion to two fingers of left hand and two fingers of right hand.

FIG. 11B is a graph illustrating average intensity vs. time curve of 12 seconds (60 fps) image sequence of two fingers of left hand and two fingers of right hand (aggregate from all four fingers) of FIG. 11A.

FIG. 11C is a graph illustrating standard EKG and peripheral oxygen saturation pulsatility data acquired simultaneous with the image sequence in accordance with embodiments of the present inventive concept.

FIG. 15A is an image illustrating LSI-analyzed velocity map of perfusion to two fingers of left hand and two fingers of right hand.

FIG. 15B is a graph illustrating average intensity vs. time curve of 12 seconds (60 fps) image sequence of two fingers of left hand and two fingers of right hand (aggregate from all four fingers).

FIG. 15C is a graph illustrating standard EKG and peripheral oxygen saturation pulsatility data acquired simultaneous with the image sequence in accordance with embodiments of the present inventive concept.

FIG. 17A is an image illustrating LSI-analyzed velocity map of perfusion to two fingers of left hand and two fingers of right hand.

FIG. 17B is a graph illustrating average intensity vs. time curve of 12 seconds (60 fps) image sequence of two fingers of left hand and two fingers of right hand (aggregate from all four fingers).

FIG. 17C is a graph illustrating standard EKG and peripheral oxygen saturation pulsatility data acquired simultaneous with the image sequence in accordance with embodiments of the present inventive concept.

FIGS. 25A and 25B are graphs illustrating time-domain (or spectral) analysis of MetaKG signals in accordance with some embodiments of the present inventive concept.

FIGS. 26A and 26B are graphs illustrating frequency-domain (or spectral) analysis of MetaKG signals in accordance with some embodiments of the present inventive concept.

FIGS. 27A and 27B are graphs illustrating Frequency-time domain (or spectrogram) analysis of MetaKG signals in accordance with some embodiments of the present inventive concept.

FIGS. 31A through 31G are images and graphs illustrating various physiologic status parameters that may be determined from a MetaKG in accordance with some embodiments of the present inventive concept.

DETAILED DESCRIPTION OF SOME EMBODIMENTS

Figure 1:
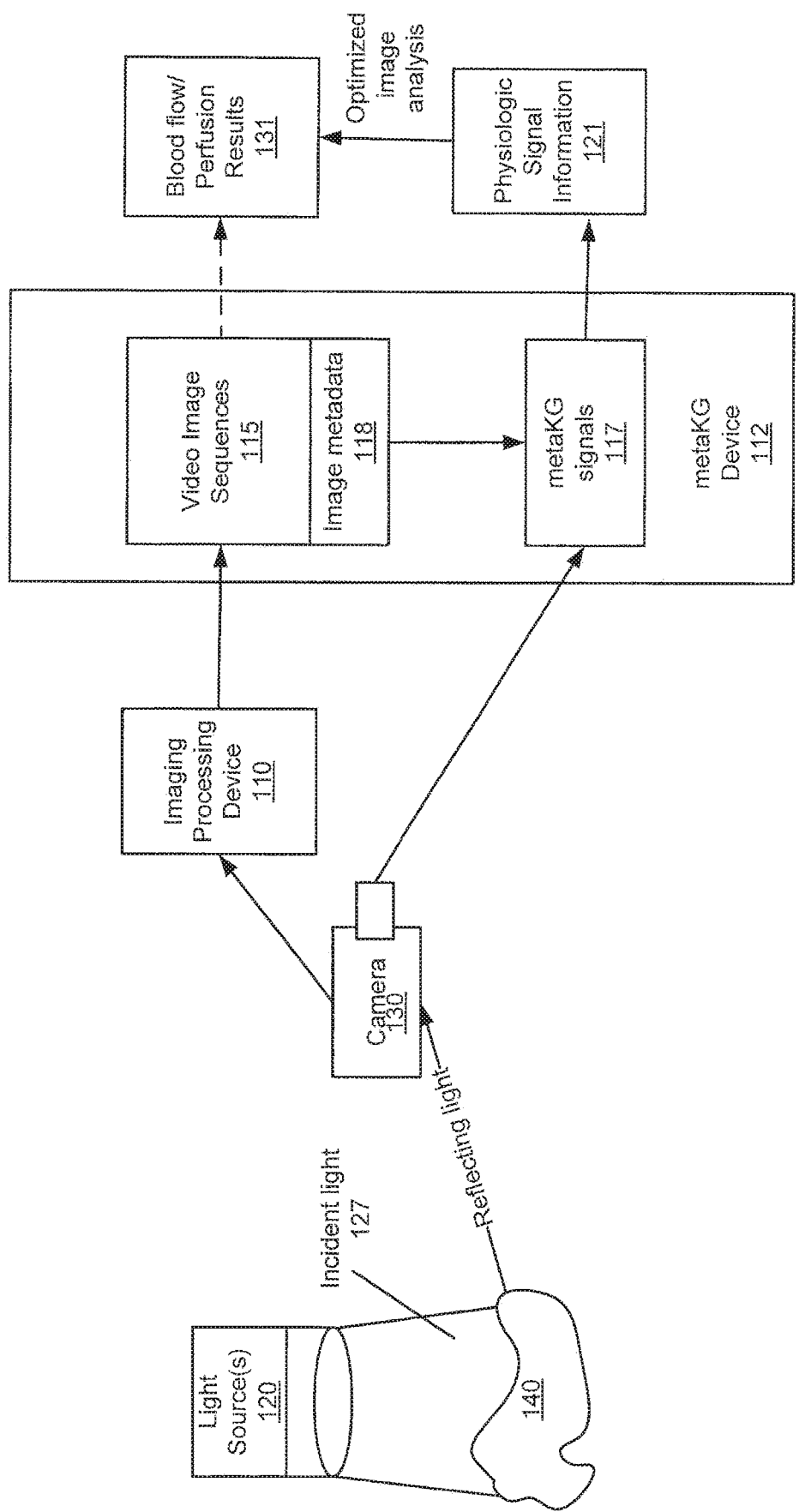
FIG. 1 is a block diagram of a system in accordance with some embodiments of the present inventive concept(s).

Specific example embodiments of the inventive concept now will be described with reference to the accompanying drawings. This inventive concept may, however, be embodied in many different forms and should not be construed as limited to the embodiments set forth herein; rather, these embodiments are provided so that this disclosure will be thorough and complete, and will fully convey the scope of the inventive concept to those skilled in the art. In the drawings, like numbers refer to like elements. It will be understood that when an element is referred to as being "connected" or "coupled" to another element, it can be directly connected or coupled to the other element or intervening elements may be present. As used herein the term "and/or" includes any and all combinations of one or more of the associated listed items.

The terminology used herein is for the purpose of describing particular embodiments only and is not intended to be limiting of the inventive concept. As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the specification and the relevant art and will not be interpreted in an idealized or overly formal sense unless expressly so defined herein.

Throughout the present application the more clinically intuitive terms "blood flow" and "perfusion" will be used to discuss aspects of the present inventive concept are used instead of the more technically oriented term "fluid velocity." However, it will be understood that these terms may be used interchangeably.

As discussed above, currently there is no method or system for direct measurement and quantification of blood flow and perfusion in real time. Accordingly, embodiments of the present inventive concept relate generally to using image metadata as a physiologically-relevant signal for any blood velocity imaging technology and analysis of that imaging technology product. As used herein, "metadata" refers to data that describes another form of data. For example, an image, as discussed herein, may include metadata that describes how large the picture is, the color depth, the image resolution, when the image was created, and other data. A text document's metadata may contain information about how long the document is, who the author is, when the document was written, and a short summary of the document. Embodiments of the present inventive concept are directed to abstracting a surrogate "metaKG" signal from any blood velocity imaging technology and analysis of that imaging technology product, by calculating an average intensity vs. time curve within a region of interest (ROI) as will be discussed further herein.

Embodiments of the present inventive concept may be applied to imaging technology, using one or more appropriate wavelengths to collect digital image data for use in a medical experimental or clinical context. The imaging may be used for simple visualization or for more complex qualitative physiologic evaluation or even more complex quantitative physiologic evaluation without departing from the scope of the present inventive concept.

Due to its physiologic dependence on the cardiac cycle, blood flow and perfusion measurement over time does not provide meaningful information without a specific indication of the cardiac phase. In cardiac computerized tomography (CT) and magnetic resonance imaging (MRI) scanning, use of the standard external electrocardiogram (EKG) to gait signal acquisition and to track time during the image acquisition gives the advantage of linking each specific blood flow and perfusion distribution to its cardiac phase. Embodiments of the present inventive concept provide methods for generating reliable instantaneous blood flow and perfusion distribution at any time of a cardiac cycle and average blood flow and perfusion distribution of several cardiac phases or cycles. Furthermore, embodiments of the present inventive concept may allow a valid comparison of blood flow and perfusion distribution in different cardiac phases and in a pre- and post-treatment fashion.

In particular, in accordance with embodiments discussed herein, when an external EKG signal is absent during the imaging process, a "surrogate EKG signal" (interchangeably referred to hereinafter as a "metaKG" signal or a "MetaKG" signal) can be calculated from the metadata contained within the image/image sequence. For example, from the average intensity vs. time curve of a specific ROI on the image sequence, using frequency component analysis, a "metaKG" signal can be calculated and may yield the same heart rate/pulsatility as an external EKG signal. The "metaKG" signal may also reflect dynamic physiology; for example, when the blood vessel is occluded, the frequency component changes compared with the frequency component of the non-occluded control state.

By using each pixel as a field of view (FOV), a two dimensional (2D) rate map can be generated using the above concept and abnormal tissue can be identified by examining the frequency component of each specific region.

Although discussed herein with respect to cardiac tissue, the "metaKG" signal calculated in accordance with embodiments of the present inventive concept is not limited to cardiac tissue. It may be calculated and used in all tissue/organ systems where blood flow and perfusion can be imaged and measured, including skin.

Thus, the metaKG signal in accordance with embodiments of the present inventive concept is a multi-channel physiological signal that can be derived from the NIR image data sequence. The number of channels can be up to the pixel number of the NIR image. As discussed above, this physiological signal can not only be used as a surrogate EKG signal, but also contains other information about the physiological condition of the monitored tissue/organ.

As discussed above, in accordance with some embodiments, average intensity within a region of interest (ROI)/multiple ROIs on the NIR image data sequence may be calculated at each time point. After a series of signal processing, such as noise removal, baseline correction and other modification, the average intensity vs. time curve at each ROI/multi ROIs is analyzed in time, frequency and time-frequency domain to monitor the physiological condition of a tissue/organ.

Thus, embodiments of the present inventive concept provide a completely non-contact, non-invasive tissue/organ physiological condition monitoring technology that can be used in real time. The monitoring region and number of channels are much less limited than traditional monitoring technology, such as EKG. This technology captures and analyzes much more information than the current products that count heart beat and pulsatility using visible light as will be discussed further herein with respect to FIGS. 1 through 31.

Referring now to FIG. 1, a system for calculating a MetaKG signal in accordance with some embodiments of the present inventive concept will be discussed. It will be understood that some systems in accordance with embodiments of the present inventive concept may be non-invasive. As used herein, "non-invasive" refers to a system or method that does not require the subject to be injected with a dye, penetrated with an object or touched with an intrabody probe or probes. Thus, as used herein, the term non-invasive refers to a system or method that makes no direct contact with the subject. As used herein, "subject" refers to the person or thing being imaged. The subject can be any subject, including a veterinary, cadaver study or human subject. As used herein, "perfusion" refers to blood flow at the tissue perfusion distribution level detected with speckle imaging.

As illustrated in FIG. 1, the system 100 includes at least one light source 120, a camera 130, an image processing device 110 and a metaKG device 112. Although the system of FIG. 1 is depicted as only including these elements, it will be understood that other elements may also be present in the system without departing from the scope of the present inventive concept. In particular, in some embodiments of the present inventive concept, multiple light sources 120 may be used. In these embodiments, the first light source may be a NIR light source and the second light source may be a visible light (VL) light source. Although embodiments of the present inventive concept are discussed herein as having one or two light sources, it will be understood that more than two light sources may also be used without departing from the scope of the present inventive concept.

In these embodiments, the NIR light source may have a wavelength of from about 780 nm to about 2500 nm and the visible light source has a wavelength of from about 400 nm to about 780 nm. Thus, some embodiments of the present inventive concept provide a system that uses two wavelengths of differential transmittance through a sample to apply LSI and/or LDI. For example, a first of the two wavelengths may be within the visible range that has zero or very shallow penetration, such as blue light 450-495 nm. This wavelength captures the anatomical structure of tissue/organ surface and serves as a position marker of the sample but not the subsurface movement of blood flow and perfusion. A second wavelength may be in the near Infra-Red (NIR) range, which has much deeper penetration. This wavelength reveals the underlying blood flow physiology and correlates both to the motion of the sample and also the movement of blood flow and perfusion. Using the imaging measurement of the visible light as a baseline, the true motion of blood flow and perfusion can be derived from the NIR imaging measurement without being affected by the motion artifact of the target. Furthermore, the anatomical structure information captured by visible light and the physiological characteristics measured by NIR light are combined. Details with respect to systems using two wavelengths are discussed in detail in U.S. Provisional Application No. 62/136,010, filed Mar. 20, 2015, the disclosure of which was incorporated herein by reference above. Although embodiments are discussed herein with respect to NIR raw images and visible light images, embodiments of the present inventive concept are not limited to this configuration. Any other image form that can adequately represent anatomy can be used without departing from the scope of the present inventive concept.

Referring again to FIG. 1, in some embodiments, the at least one light source unit 120 may be, for example, one or more lasers or light emitting diode (LED) lights. The at least one light source 120 may be used to illuminate a region of interest 140 (hereinafter "tissue/organ"). If the light source 120 is an NIR light source, it may have a wavelength of from about 780 nm to about 2500 nm. As used herein, the "region of interest" refers to the region of the subject that is being imaged, for example, the principal vessels and tissue, organs, etc. When light (incident light 127) from the at least one source 120 is directed to a living target (region of interest 140), such as a tissue/organ, part of the light will go through multiple scattering inside the target and eventually reflect back (Reflecting light) to the camera 130 as shown in FIG. 1.

The camera 130 is configured to collect the reflecting light and provide a visible light or NIR image (NIR Layer 115), each with different characteristics depending, for example, upon a depth of penetration of the illumination light determined by the wavelength energy. Thus, laser illumination 120 and image capture 130 may be processed 110 with near-infrared (NIR) technology and results in a video image sequence or sequences 115 for subsequent analysis. Details with respect to the NIR technology is discussed in commonly assigned International Application No. PCT/US2015/055251, entitled Methods, Systems and Computer Program Products for Visualizing Anatomical Structures, Blood Flow and Perfusion Using Near-Infrared Imaging, filed concurrently herewith, the contents of which are hereby incorporated herein by reference as if set forth in its entirety.

Contained within this image sequence or sequences 115 is metadata 118 associated with the each image sequence or sequences. The metaKG device 112 according to embodiments of the present inventive concept processes the metadata 118 associated with the image sequences and provides a "metaKG signal" 117, which directly links to underlying fundamental physiologic and/or pathophysiologic processes 121 being imaged. In accordance with embodiments discussed herein, the metaKG signals can optimize the image acquisition and may be integral to optimizing analysis of blood flow and perfusion 131. Since the metaKG signal 117 is imbedded in the metadata 118 of the non-invasively acquired image sequence without direct tissue contact, embodiments of the inventive concept of the metaKG enables this new image approach to be directly linked to the physiologic and pathophysiologic 121 parameters and characteristics without the requirement for traditional external EKG signals. Thus, a sample 140, for example, tissue or organ, with blood flow and perfusion may be examined for measurement and quantification of blood flow and perfusion 131 using non-invasive imaging, with no need for an EKG.

As discussed above, in a multi-wavelength embodiment, the region of interest 140 is illuminated with two different light sources, for example, NIR and VL, and two sets of images are acquired and processed to obtain two different types of metadata, for example, NIR-metadata and VL-metadata. Accordingly, the calculations discussed herein with respect to metadata related to a single wavelength may be performed for multiple wavelength data. For example, the NIR MetaKG and the VL MetaKG may be calculated from the metadata, a movement-related common signal component may be extracted from the NIR MetaKG and the VL MetaKG; and a noise-free MetaKG may be calculated by cancelling out the movement-related common signal component from the NIR MetaKG as will be discussed further below with respect to a single wavelength. In other words, using two wavelengths in accordance with some embodiments discussed herein may improve the signal to noise ratio (SNR) of the image by combining the penetrating capability of the NIR wavelengths and the advantages of the VL wavelengths, i.e. the superficial surface noise of the VL may be cancelled out.

Figure 2A:
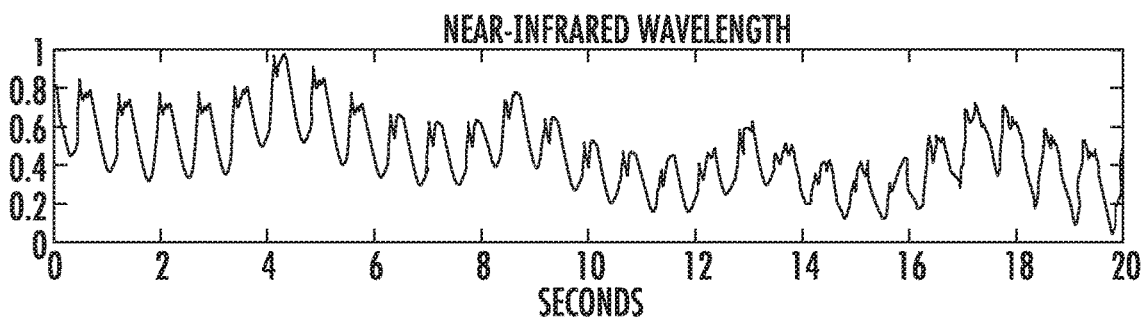
FIGS. 2A through 2C are graphs illustrating average intensity vs. time in a multi-wavelength imaging technology in accordance with some embodiments of the present inventive concept.
Figure 2B:
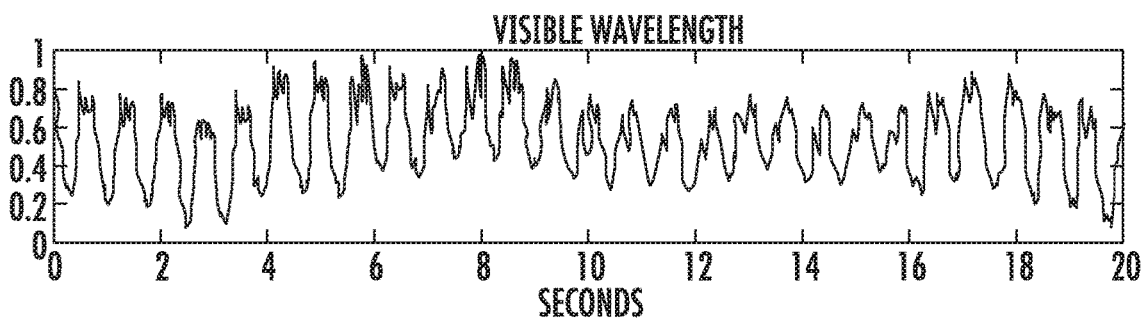
Figure 2C:
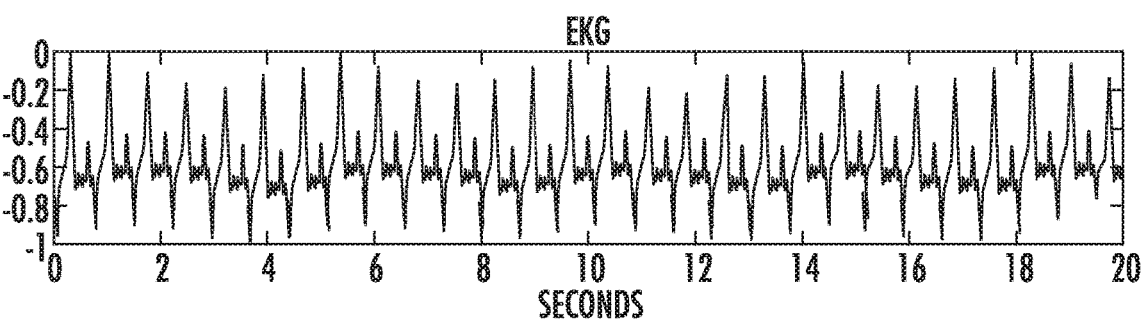

Referring now to FIGS. 2A through 2C, graphs illustrating average intensity vs. time using a multi-wavelength imaging technology to document the presence of the metaKG signal will be discussed. FIG. 2A illustrates the 20 seconds metaKG using near infra-red wavelength illumination; FIG. 2B illustrates the 20 seconds metaKG using near visible wavelength illumination; and FIG. 2C illustrates the 20 seconds EKG signals. As illustrated therein, the metaKG is fluctuating at heart rate frequency (90 peaks per minute) and also at respiration frequency (one larger peak every 4-5 seconds). FIGS. 2A through 2C also illustrate that the metaKG generated by near infra-red illumination has less noise than the one generated by visible wavelength illumination.

Figure 3A:
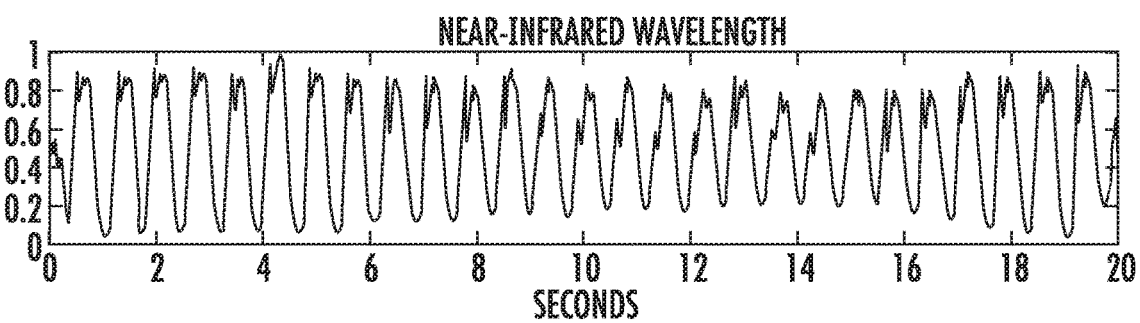
FIGS. 3A through 3C are graphs illustrating average intensity vs. time in a multi-wavelength imaging technology having respiration contamination removed in accordance with some embodiments of the present inventive concept.
Figure 3B:
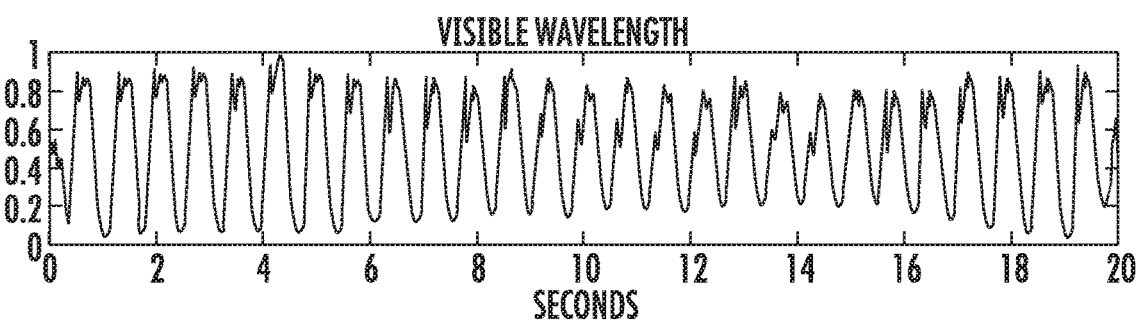
Figure 3C:
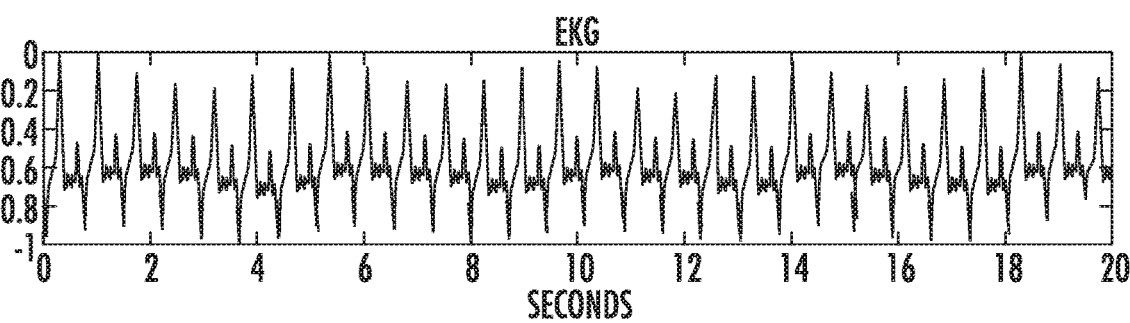

Referring now to FIGS. 3A through 3C, graphs illustrating average intensity vs. time using a multi-wavelength imaging technology to document the presence of the metaKG signal with respiration contamination removed will be discussed. FIG. 3A illustrates the 20 seconds metaKG without respiration contamination using near infra-red wavelength illumination; FIG. 3B illustrates the 20 seconds metaKG without respiration contamination using near visible wavelength illumination; and FIG. 3C illustrates the 20 seconds EKG signals. As illustrated in FIGS. 3A through 3C, the metaKG is only fluctuating at heart rate frequency (90 peaks per minute). As further illustrated, the metaKG generated by near infra-red illumination has less noise than the one generated by visible wavelength illumination.

Thus, it will be understood that although many embodiments of the present inventive concept are discussed herein with respect to a single light source having a particular wavelength, embodiments of the present inventive concept are not limited to this configuration.

FIGS. 4A through 4C are images illustrating a single frame in the raw image data sequence (4A); inversed spatial contrast image (4B) and an inversed temporal contrast image (4C). The graph of FIG. 5 illustrates average intensity vs. time during the image acquisition period of time as the metaKG signal (end-diastolic phase in a specific cardiac cycle is labeled). Thus, FIGS. 4A through 4C and 5 illustrate instantaneous blood velocity distribution of anterior wall of a heart using Laser Speckle Imaging (LSI) at the end-diastolic phase of the cardiac cycle (determined visually).

FIGS. 6A through 6C illustrate a single frame in the raw image data sequence (6A); an inversed spatial contrast image (6B); and an inversed temporal contrast image (6C). FIG. 7 illustrates an average intensity vs. time curve during the image acquisition period of time as the metaKG signal (end-diastolic phase in nine (9) cardiac cycles are used). Thus, FIGS. 6A through 6C and 7 illustrate average blood velocity distribution of anterior wall of a heart using Laser Speckle Imaging at the end-diastolic phase of the cardiac cycle.

FIGS. 8A through 8C illustrate a single frame in the raw image data sequence (8A); an inversed spatial contrast image (8B); and an inversed temporal contrast image (8C). FIG. 8D illustrates an average intensity vs. time curve during the image acquisition period of time as the metaKG signal (end-systolic phases in eight (8) cardiac cycles are used). Thus, FIGS. 8A through 8D illustrate average blood velocity distribution of anterior wall of a heart using Laser Speckle Imaging at the end-systolic phase of the cardiac cycle (determined visually).

Figure 9A:
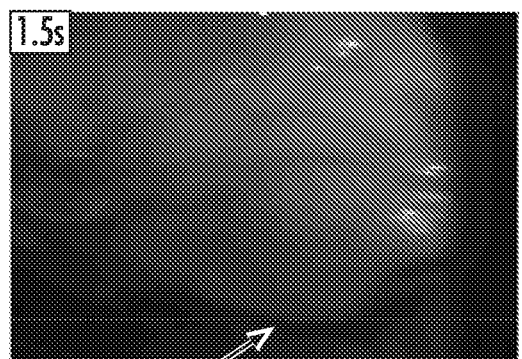
FIG. 9A is an image illustrating one frame of raw image data sequence in diastolic phase.
Figure 9B:
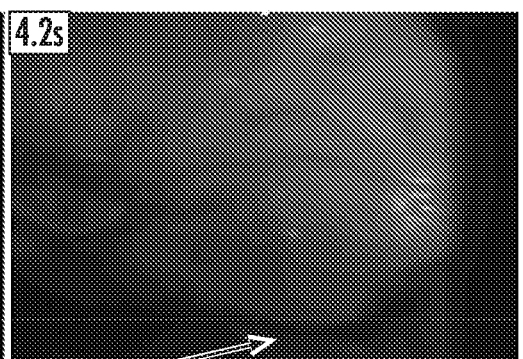
FIG. 9B is an image illustrating one frame of raw image data sequence in systolic phase.
Figure 9C:
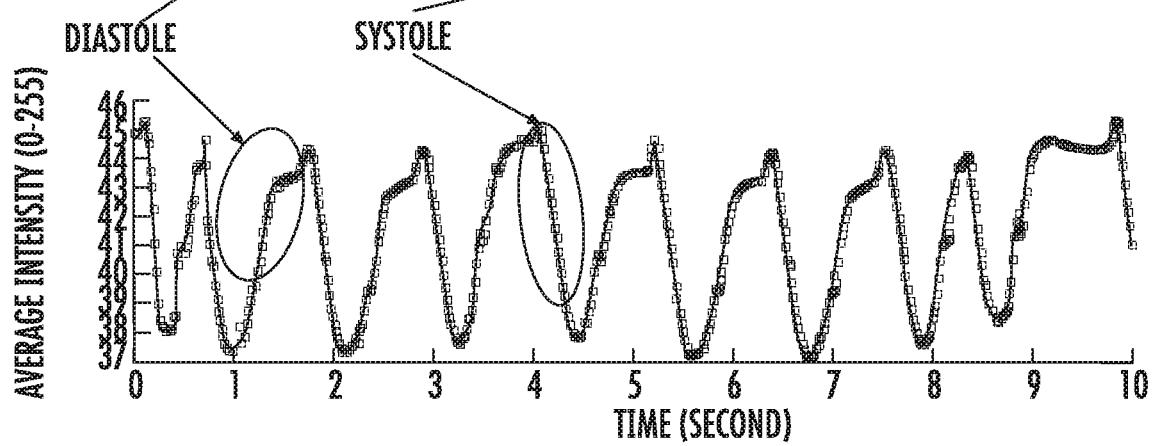
FIG. 9C is a graph of average intensity vs. time curve as the metaKG signal in accordance with some embodiments of the present inventive concept.

FIGS. 9A through 9B illustrate using an average intensity vs. time curve as the metaKG signal in a potential cardiac application to assess blood flow and perfusion. FIG. 9C illustrates the average intensity vs. time curve as the metaKG signal with diastolic and systolic phases labeled. FIG. 9A illustrates one frame of raw image data sequence in diastolic phase and FIG. 9B illustrates one frame of raw image data sequence in systolic phase.

Figures 10A, 10B:
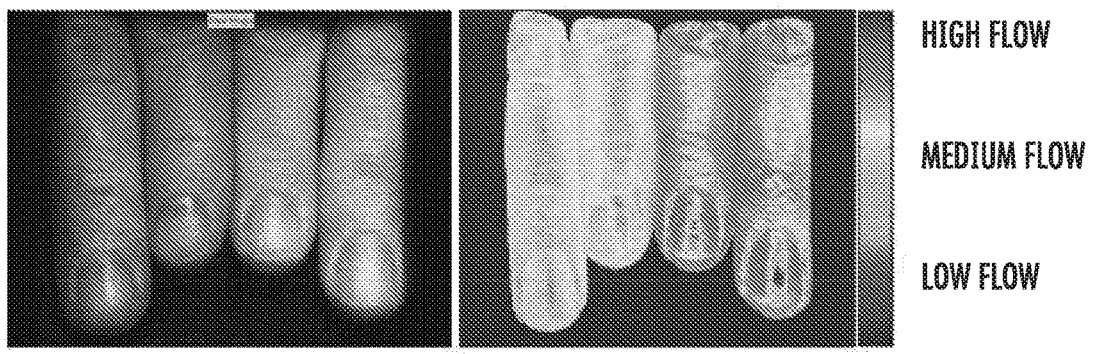
FIG. 10A is an image illustrating one frame from raw image data sequence.
FIG. 10B is an image illustrating the blood velocity distribution in the fingers.
Figure 10C:
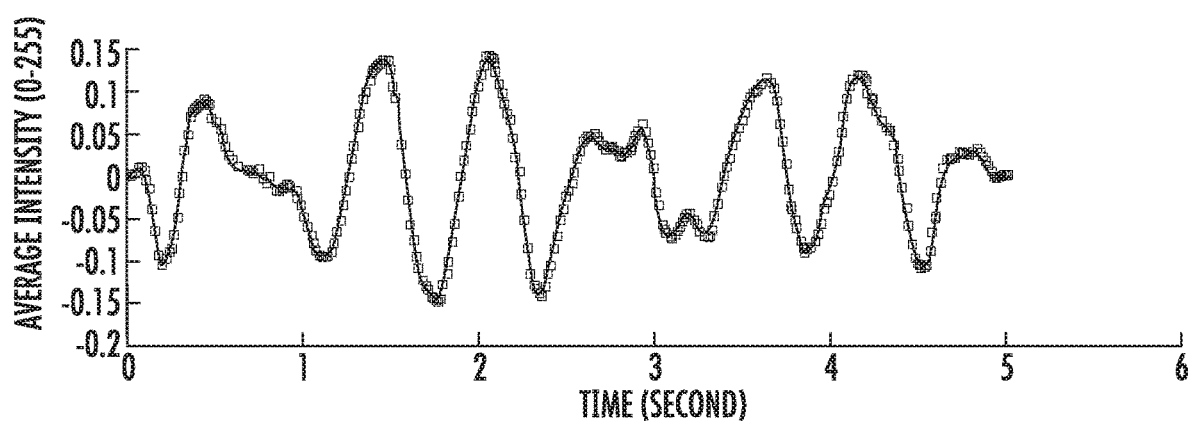
FIG. 10C is a graph of average intensity vs. time curve as the metaKG signal in accordance with some embodiments of the present inventive concept.

Referring now to FIGS. 10A through 10C, using average intensity vs. time curve as the metaKG signal in a potential skin/peripheral extremity application to assess blood flow and perfusion will be discussed. FIGS. 10A and 10B illustrate a finger perfusion measurement setup. FIG. 10A illustrates one frame from raw image data sequence, with flow to the two left fingers reduced by greater than 70% by inflation of a blood pressure cuff on the left arm. FIG. 10B illustrates the blood velocity distribution, illustrating this substantial reduction in flow and perfusion to the left fingers. FIG. 10C is a graph illustrating an average intensity vs. time curve as the metaKG signal.

Referring to FIGS. 11A through 18H, use of the average intensity vs. time curves as the metaKG signal in a different finger perfusion measurement experiment will be discussed. These figures illustrate a potential skin/peripheral extremity application to assess blood flow and perfusion. The figures document the interoperability of the metaKG, the external standard EKG, flow, velocity of flow, frequency, and change in frequency due to pathophysiologic changes in flow and perfusion in accordance with embodiments discussed herein.

Referring first to FIGS. 11A through 11C, embodiments of at baseline, with no fingers occluded will be discussed. FIG. 11B illustrates the average intensity vs. time curve of 12 seconds (60 fps) image sequence of two fingers of left hand and two fingers of right hand (aggregate from all four fingers). FIG. 11A illustrates an LSI-analyzed velocity map of perfusion to all four fingers. FIG. 11C illustrates standard EKG and peripheral oxygen saturation pulsatility data acquired simultaneous with the image sequence. The metaKG 'rate' is 73 beats/min (bpm), while the recorded standard EKG rate is 74 bpm.

Figure 12A:
FIGS. 12A and 12B illustrate the two left fingers of FIG. 11A and the associated average intensity vs. time curve of the two left fingers.
Figure 12C:
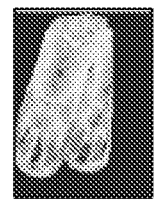
FIGS. 12C and 12D illustrate the two right fingers of FIG. 11A and the associated average intensity vs. time curve of the two right fingers.
Figure 12B:
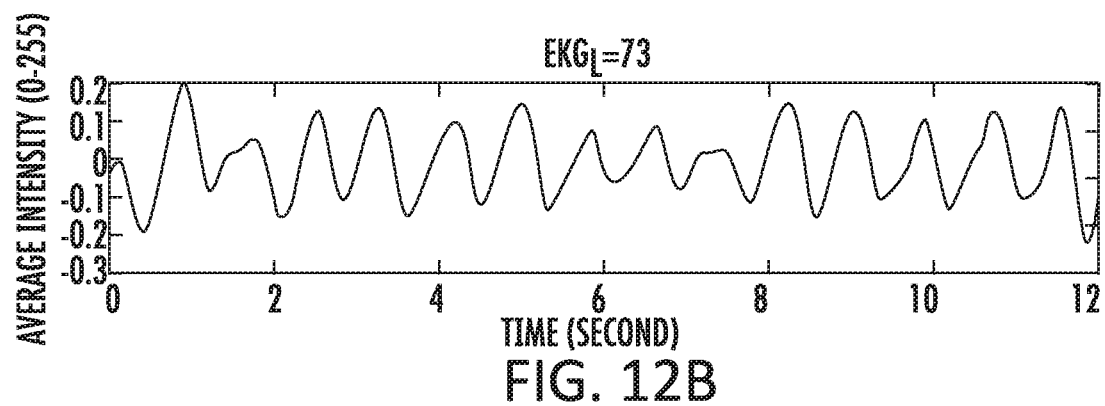
Figure 12D:
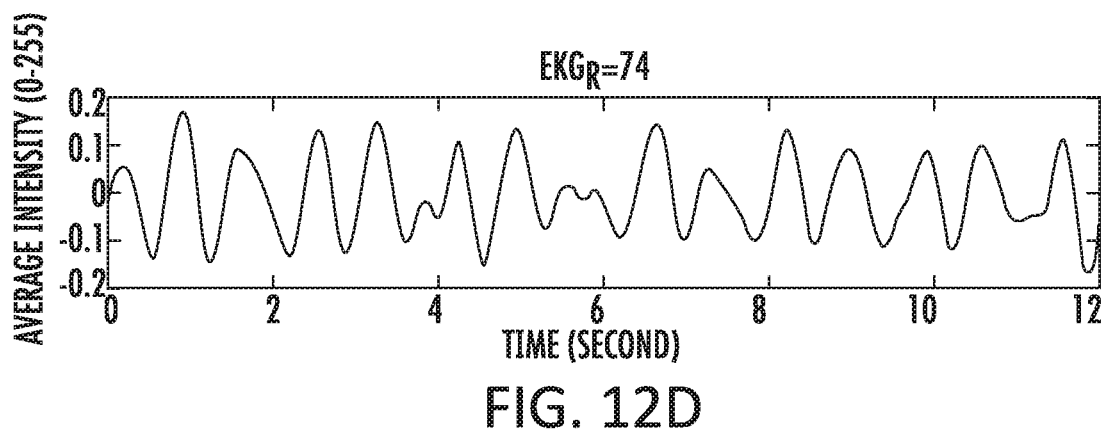
Figure 12E:
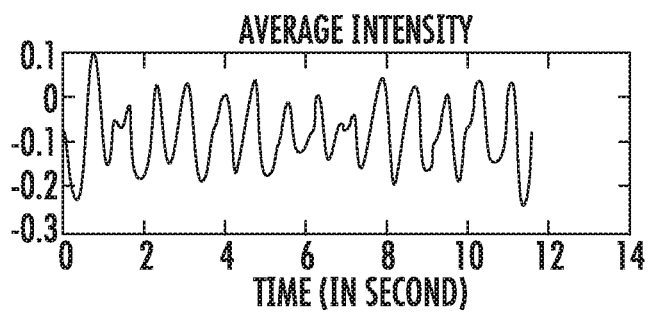
FIGS. 12E through 12H are graphs illustrating frequency domain analyses of the average intensity vs. time curves for both the left (E and F) and right (G and H) fingers.
Figure 12F:
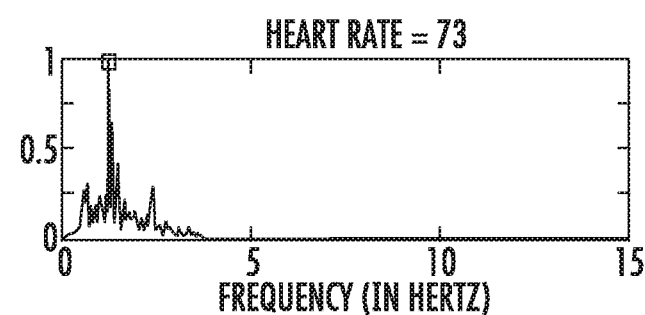
Figure 12G:
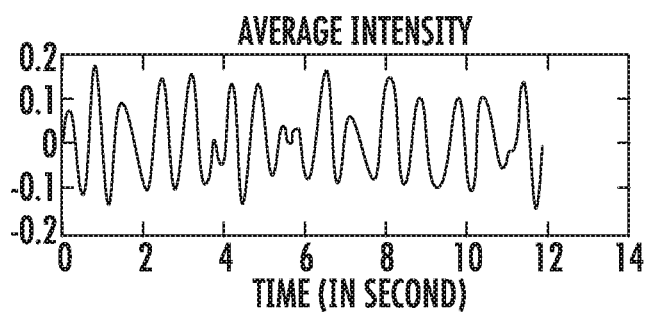
Figure 12H:
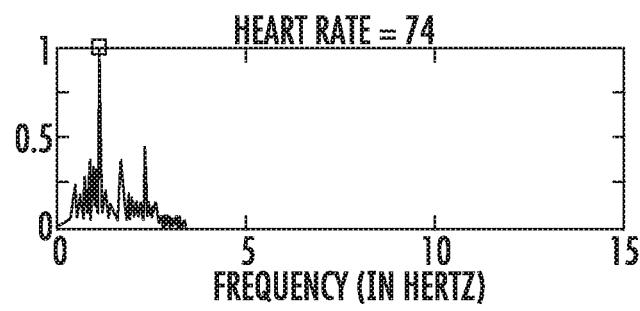

Referring now to FIGS. 12A through 12H, using the same data as in FIGS. 11A-C, this baseline data is further analyzed. FIGS. 12B and 12D illustrate the wave form of the average intensity vs. time curve of the two left (12A) and two right (12C) finger sets, respectively, and show that they are similar (L=73 bpm, R=74 bpm). FIGS. 12E/F and 12G/H are frequency domain analyses of the average intensity vs. time curves, which document that the main frequency component in both finger sets is the heart rate (HR), and that the main frequency component of the two left fingers (FIGS. 12E and 12F) and two right fingers (FIGS. 12G and 12H) are virtually identical.

Figure 13A:
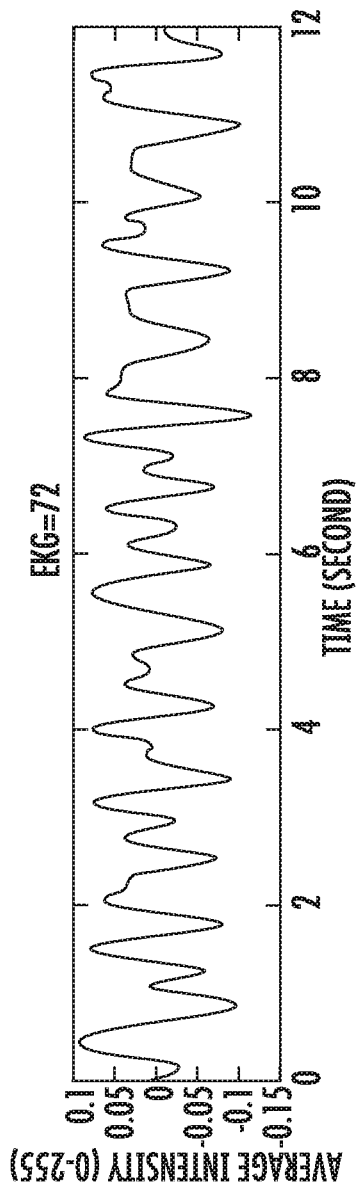
FIG. 13A is an image illustrating LSI-analyzed velocity map of perfusion to two fingers of left hand and two fingers of right hand.
Figure 13B:
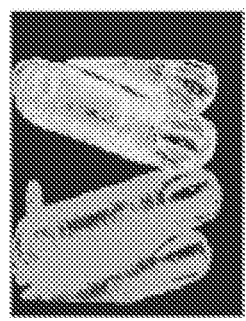
FIG. 13B is a graph illustrating average intensity vs. time curve of 12 seconds (60 fps) image sequence of two fingers of left hand and two fingers of right hand (aggregate from all four fingers) of FIG. 11A.
Figure 13C:
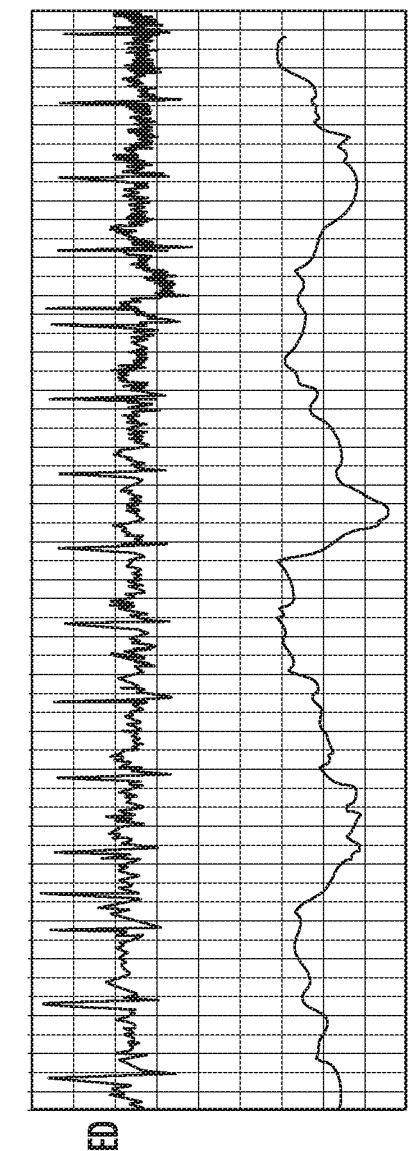
FIG. 13C is a graph illustrating standard EKG and peripheral oxygen saturation pulsatility data acquired simultaneous with the image sequence in accordance with embodiments of the present inventive concept.

Referring now to FIGS. 13A through 13C, results of the same experimental setup as FIGS. 11A-12H, but now flow and perfusion to the left two fingers (FIG. 13A) are occluded by the blood pressure cuff will be discussed. The peripheral oxygen saturation measurement is made from the third digit on the left hand. FIG. 13B illustrates an average intensity vs. time curve of 12 seconds (60 fps) image sequence of two fingers of left hand and two fingers of right hand (FIG. 13A). FIG. 13C illustrates the standard external EKG and peripheral oxygen saturation pulsatility data acquired simultaneous with the image sequence. With the finger occlusion, the metaKG signal (aggregate from all four fingers) differs slightly from the standard EKG (72 bpm vs. 69 bpm).

Figure 14A:
FIGS. 14A and 14B illustrate the two left fingers and the associated average intensity vs. time curve of the two left fingers.
Figure 14C:
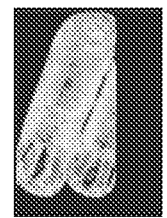
FIGS. 14C and 14D illustrate the two right fingers and the associated average intensity vs. time curve of the two right fingers.
Figure 14B:
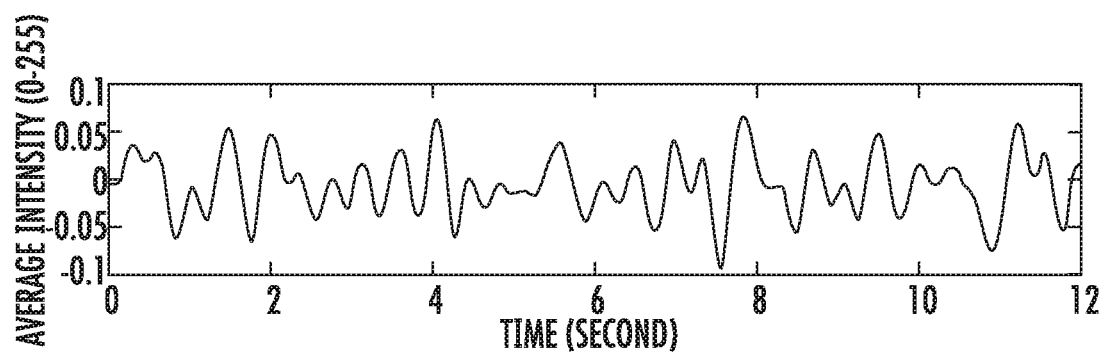
Figure 14D:
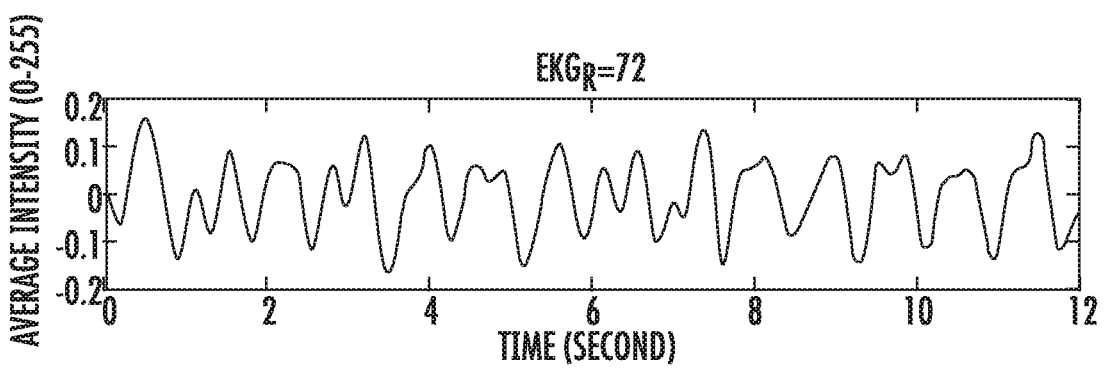
Figure 14E:
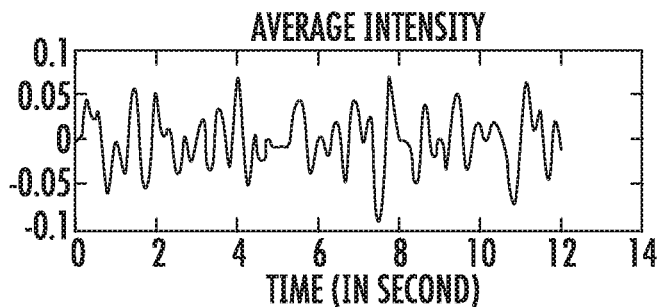
FIG. 14E through 14H are graphs illustrating frequency domain analyses of the average intensity vs. time curves for both the left (E and F) and right (G and H) fingers.
Figure 14F:
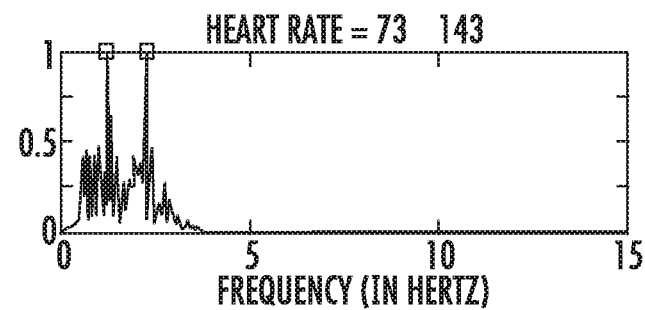
Figure 14G:
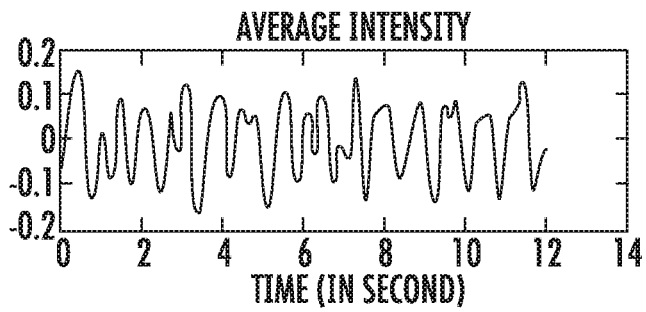
Figure 14H:
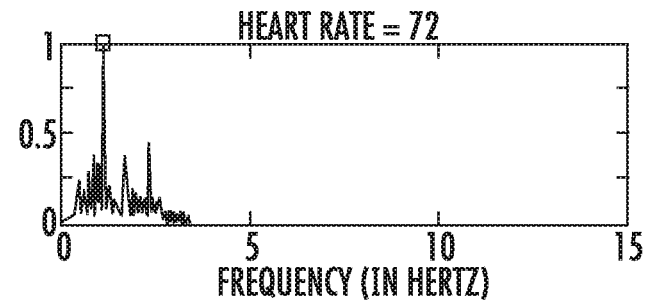

Referring now to FIGS. 14A through 14H, analysis is similar to that discussed above with respect to FIGS. 12A-H. The flow and perfusion to the left finger set (14A) are occluded, while the right finger set (14C) is normally perfused as the control. FIGS. 14B and 14D illustrates the wave form of the average intensity vs. time curve as the metaKG of the left (14B) and right finger sets (14D), and that they are different. FIGS. 14E/F and 14G/H illustrate the frequency domain analysis of the average intensity vs. time curves. FIGS. 14G/H illustrate the main frequency component of the non-occluded right finger set (14D) is still the HR. FIGS. 14E/F, however, illustrate the frequency component of the occluded left finger set is degraded from the perfused condition in FIGS. 12E/F, and very different from the frequency component of the two right fingers (FIGS. G/H). Thus, FIGS. 14A through 1414 illustrate that there is a difference in the metadata (B&D) because blood flows to the fingers in A are occluded and those in C are not. The strength of intensity fluctuation in D and G are much greater than that in B and E. In other words, when the blood flow is blocked, the metadata (MetaKG) may weaken.

Referring now to FIGS. 15A through 15C, results of the same experimental setup as prior figures, but now the blood cuff on the left arm has been released and both finger sets are perfused again (note the time stamp from the standard EKG display) will be discussed. FIG. 15B illustrates the average intensity vs. time metaKG curve of 12 seconds (60 fps) image sequence of two fingers of left hand and two fingers of right hand (FIG. 15A). FIG. 15C illustrates bottom panel is the standard external EKG and peripheral oxygen saturation pulsatility data acquired simultaneously with the image sequence. The metaKG rate is 72 bpm versus the standard EKG rate of 75 bpm.

Figure 16A:
FIGS. 16A and 16B illustrate the two left fingers and the associated average intensity vs. time curve of the two left fingers.
Figure 16C:
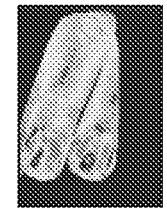
FIGS. 16C and 16D illustrate the two right fingers and the associated average intensity vs. time curve of the two right fingers.
Figure 16B:
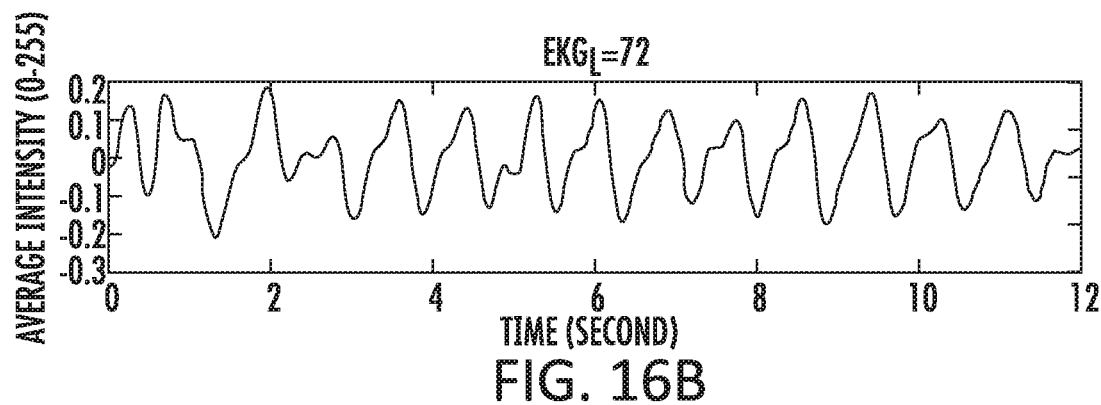
Figure 16D:
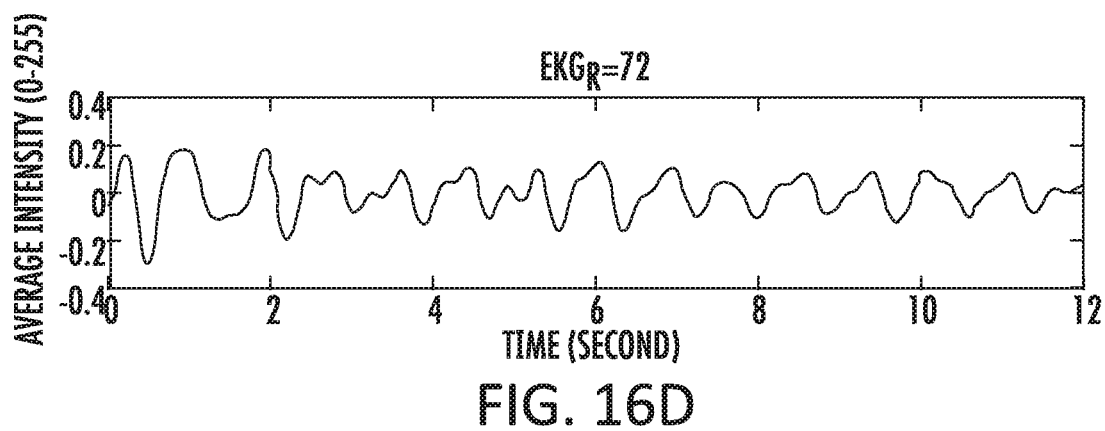
Figure 16E:
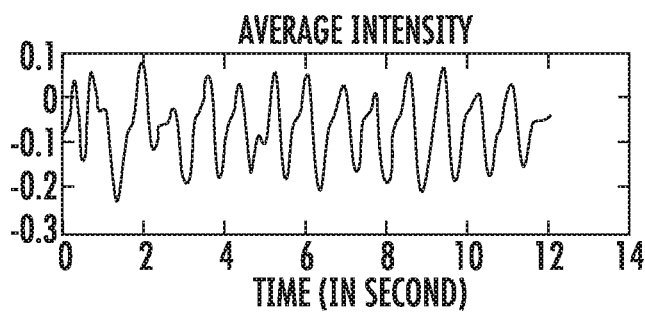
FIG. 16E through 16H are graphs illustrating frequency domain analyses of the average intensity vs. time curves for both the left (E and F) and right (G and H) fingers.
Figure 16F:
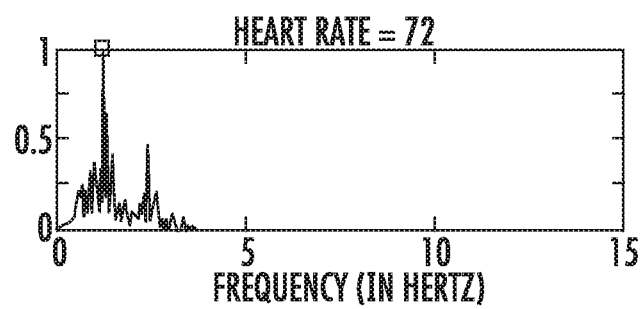
Figure 16G:
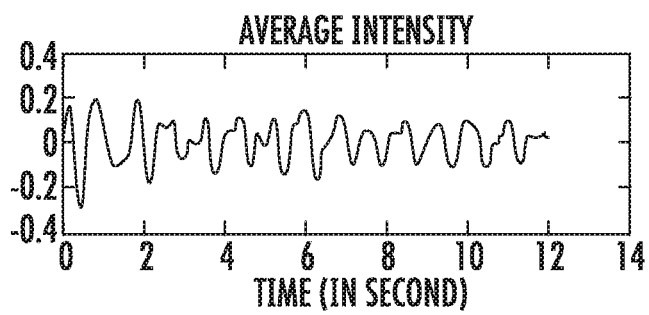
Figure 16H:
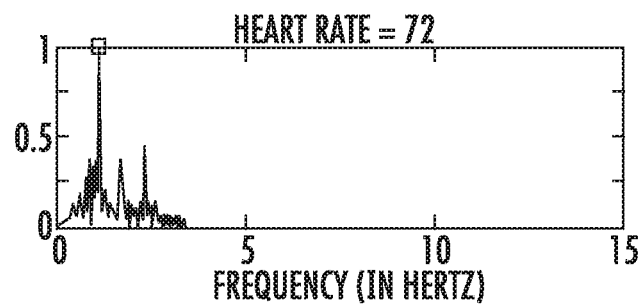

Referring now to FIGS. 16A through 16H, an analysis is similar to FIGS. 12 and 14 above will be discussed. FIGS. 16B and 16D illustrate the wave form of the average intensity vs. time curve of the left (16A) and right (16C) finger sets are similar after the occlusion on the two left fingers (16A) are released. FIGS. 16E/F and 16G/H illustrate the frequency domain analyses of the average intensity vs. time curves, which again illustrate that the main frequency component is the HR, and that the main frequency component of the left finger set (16E/F) and the right finger set (16G/H) are identical again after the occlusion to the left finger set is released.

Referring now to FIGS. 17A through 17C, using the same experimental setup as FIG. 15, the heart rate of the subject was temporarily increased by isometric exercise. The average intensity vs. time curve as the metaKG signal in this finger perfusion experiment is illustrated with the heart rate elevated. FIG. 17B is the average intensity vs. time curve of 12 seconds (60 fps) image sequence of the left and right finger sets (17A). FIG. 17C illustrates the standard external EKG and peripheral oxygen saturation pulsatility data acquired simultaneously with the image sequence.

Figure 18A:
FIGS. 18A and 18B illustrate the two left fingers and the associated average intensity vs. time curve of the two left fingers.
Figure 18C:
FIGS. 18C and 18D illustrate the two right fingers and the associated average intensity vs. time curve of the two right fingers.
Figure 18B:
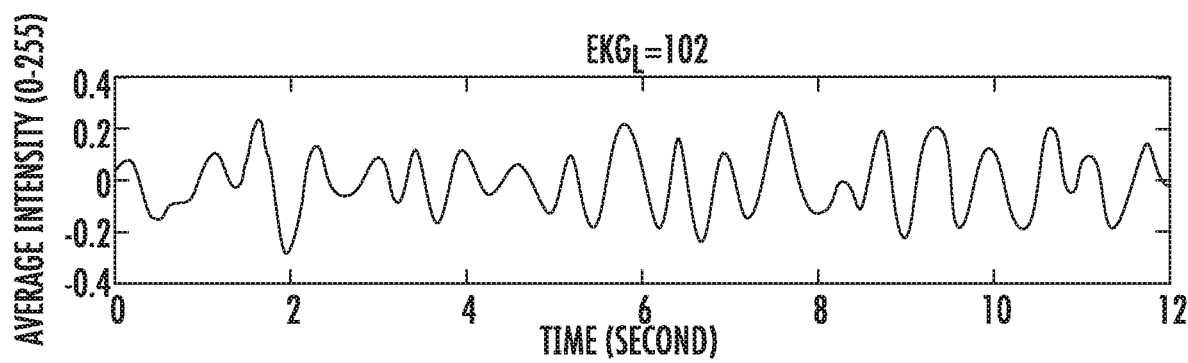
Figure 18D:
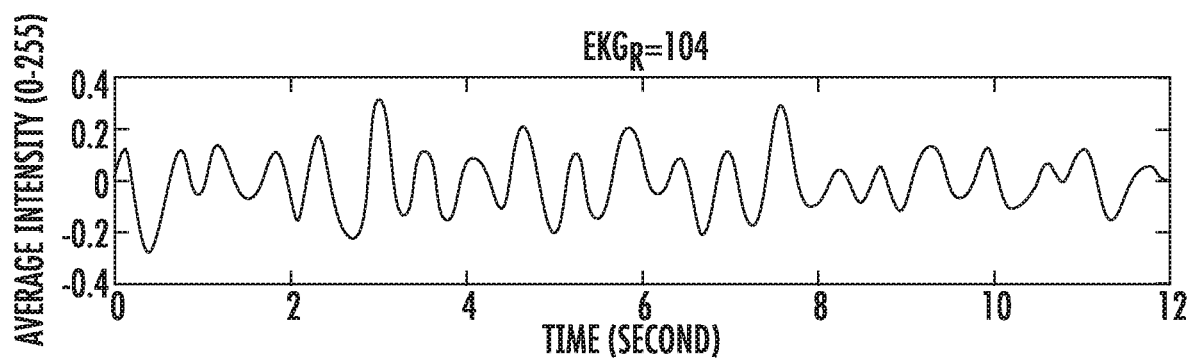
Figure 18E:
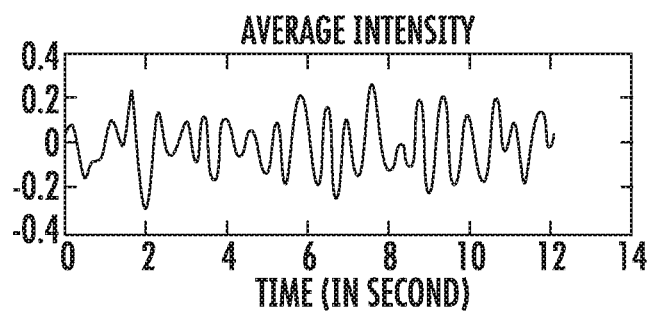
FIGS. 18E through 18H are graphs illustrating frequency domain analyses of the average intensity vs. time curves for both the left (E and F) and right (G and H) fingers.
Figure 18F:
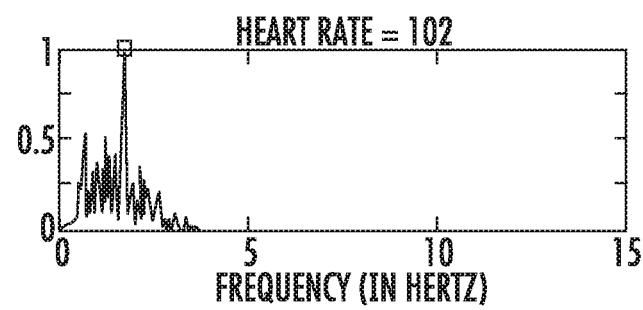
Figure 18G:
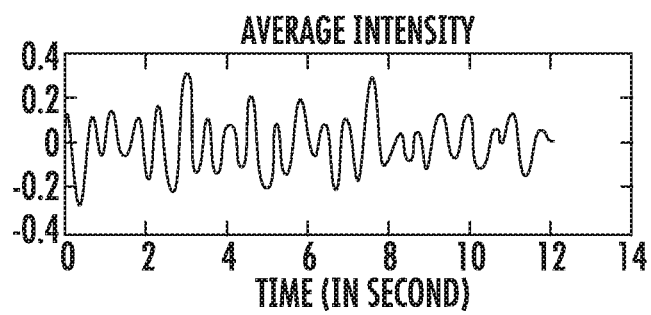
Figure 18H:
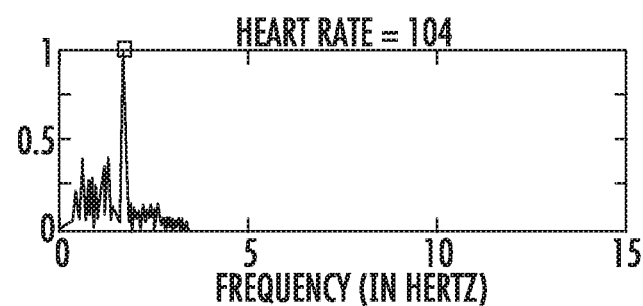

Referring now to FIGS. 18A through 18H, FIGS. 18B and 18D illustrate that wave forms of the average intensity vs. time curve of the left (18A) and right (18C) finger sets are similar. FIGS. 18E/F and 18G/H illustrate that the frequency domain analyses of the metaKG data, which show the main frequency component is the HR in both finger sets (18A and 18C), and that the main frequency component of the two left fingers (FIGS. 18E/F) and two right fingers (FIGS. 18G/H) are identical.

As discussed above, because the blood flow and perfusion are dynamic processes that change in one cardiac cycle, it is critical to synchronize the imaging measurement results with a reference signal. Most commonly in medical imaging the reference signal is the external electrocardiogram (EKG) signal. In other words, if the blood flow measurement is not linked to specific physiologic parameters, such as the time point during a cardiac cycle, the results are not useful because they have no physiologic context.

Furthermore, the significance of the physiologically-referenced, for example, EKG-timed, blood flow and perfusion measurement in evolving imaging technologies is Instantaneous flow and perfusion distribution that can be generated and linked at any time of a cardiac cycle as discussed above. Similarly, average flow and perfusion distribution can also be generated and linked to one or several cardiac phases or cycles as discussed with respect to the figures above.

The significance of the physiologically-referenced, for example, EKG-timed, blood flow and perfusion comparison, i.e., before and after an intervention, in evolving imaging technologies is as follows: (1) A standardized, non-temporal baseline for comparison (in physiology, time phase is not standard across clinical applications); and (2) unique and often novel new physiologic/pathophysiologic information, not obtainable otherwise.

The significance of the physiologically-referenced, for example, EKG-timed, blood flow and perfusion also creates the analytical basis for: (1) quantitative comparison of the instantaneous flow and perfusion distribution, because the flow and perfusion patterns will vary, based on the physiology/pathophysiology of blood flow and perfusion. Quantitative comparison typically requires before and after imaging data that are synchronously comparable, and EKG synchronization is a useful way to link the quantitative flow and perfusion to an independent, objective benchmark, i.e. a specific cardiac phase. Moreover, the precision of a benchmark like the EKG is useful for defining the starting and ending points of the averaging process, versus simply finding a random starting point and averaging a few seconds of flow and perfusion measurements, where quantitative comparison of the average flow and perfusion maps is indicated.

Embodiments of the present inventive concept address situations where an EKG signal is not available or desirable. As discussed herein, embodiments of the present inventive concept provide a "surrogate EKG signal" that can be used instead of the standard EKG signal to identify and target these physiologic processes, benchmarks, data acquisition and data analysis parameters. The "surrogate EKG signal" has been referred to herein as a "MetaKG signal." The MetaKG in accordance with embodiments discussed herein consists of an electrical, mechanical, and/or motion signal embedded in the metadata of the image file(s) obtained by imaging across or within the visible and near-infrared spectrum wavelengths. The surrogate EGK signal is referred to herein as "metaKG."

As discussed above with respect to the Figures, for example, FIGS. 2 through 8D, the metaKG is imbedded in the average intensity vs. time curve of the raw image data sequence. In particular, if 10 seconds of image sequence is captured at 100 frames/second, an average intensity is calculated at each frame to form a curve of 1000 intensity points along the 0-10 second time line. Due to contraction of the heart, the imaged tissue/organ will move toward and away from the camera causing the intensity to fluctuate periodically. The fluctuation of intensity shows a certain pattern in one cardiac cycle and repeats itself in different cardiac cycles.

Although embodiments of the present inventive concept are discussed herein with respect to cardiac applications, embodiments of the present inventive concept are not limited to this configuration. For example, the periodic fluctuation average intensity vs. time not only happens in cardiac imaging applications, but also in other tissues/organs. In particular, FIGS. 10A through 10C illustrate a metaKG signal in accordance with embodiments discussed herein from finger digits of the upper extremities, despite being located quite far from the heart.

In validating the accuracy of this metaKG physiologic data using frequency component analysis, in FIGS. 11A through 11C, the metaKG signal yields the same heart rate as the real EKG signal and peripheral oxygen saturation pulsatility data (73 bpm vs. 74 bpm).

As further illustrated in FIGS. 12A through 12H, the frequency components of the average intensity vs. time curves from representative different normal tissues (left hand finger pair (12A) vs. right hand finger pair (12C)) are similar indicating the HR as the main frequency component of the metaKG.

As evidence of the physiologic relevance of the metaKG, when blood flow and perfusion are physiologically or pathophysiologically reduced, the frequency component of the average intensity vs. time curve metaKG from the occluded tissue changes compared with the frequency component from the non-occluded control tissue metaKG, as illustrated in FIGS. 13A-C. In FIGS. 14A through 14H, the main frequency component of the metaKG average intensity vs. time curve from the non-occluded control tissue is still the HR which is consistent with the external EKG reading while the frequency component of average intensity vs. time curve from the occluded tissue becomes more complex. This indicates the presence of a different and abnormal underlying physiological response.

As further evidence of the physiologic relevance of the metaKG, when blood flow and perfusion can be restored to the certain part of tissue that was previously interrupted of blood flow and perfusion, the frequency components of the average intensity vs. time metaKG from occlusion released tissue and normal tissue are similar, as indicated by the HR as the main frequency component as shown in FIGS. 15A through 15C and 16A through 16H.

Finally, as further evidence of the physiologic relevance of the metaKG, FIGS. 17A through 17C and 18A through 18H demonstrate that when the heart rate is elevated (HR 103 bpm), the frequency components of the average intensity vs. time metaKG curves from different normal tissues are similar. This indicates that metaKG signal HR is the main frequency component, which again is consistent with the external EKG tracing obtained at the same time.

Accordingly, as discussed briefly above, using an EKG signal to track time during the image acquisition is useful to link each specific blood flow and perfusion distribution to its cardiac phase. For any blood flow and perfusion imaging technology, this method can generate reliable instantaneous blood flow and perfusion distribution at any time of a cardiac cycle and average blood flow and perfusion distribution of several cardiac phases or cycles. Furthermore, this method allows the valid comparison of blood flow and perfusion distribution in different cardiac phases and in a pre and post treatment fashion. Thus, the link between EKG and image acquisition and subsequent instantaneous and average blood flow and perfusion measurement upgrades any current blood flow and perfusion imaging technology into a more practical, reliable, precise and clinically relevant methodology. In accordance with embodiments discussed herein, when an EKG signal is absent during the imaging process, a metaKG signal (surrogate EKG signal) can be calculated from the average intensity vs. time curve of a specific region of interest on the image sequence. As discussed above with respect to FIGS. 2 through 18H, the metaKG signal yields reliable heart rate/pulsatility information using frequency component analysis. When the blood vessel is occluded, the frequency component changes compared with the frequency component of the non-occluded control tissue indicating underlying physiological response.

Figure 19:
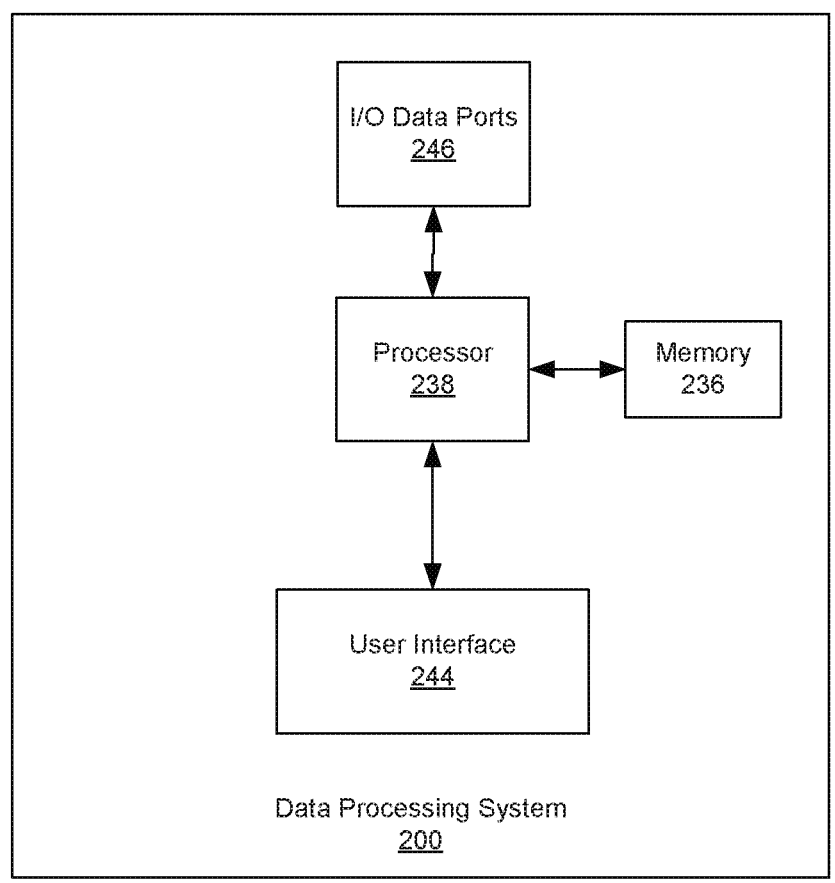
FIG. 19 is a block diagram of a data processing system according to embodiments of the present inventive concept(s).
Figure 20:
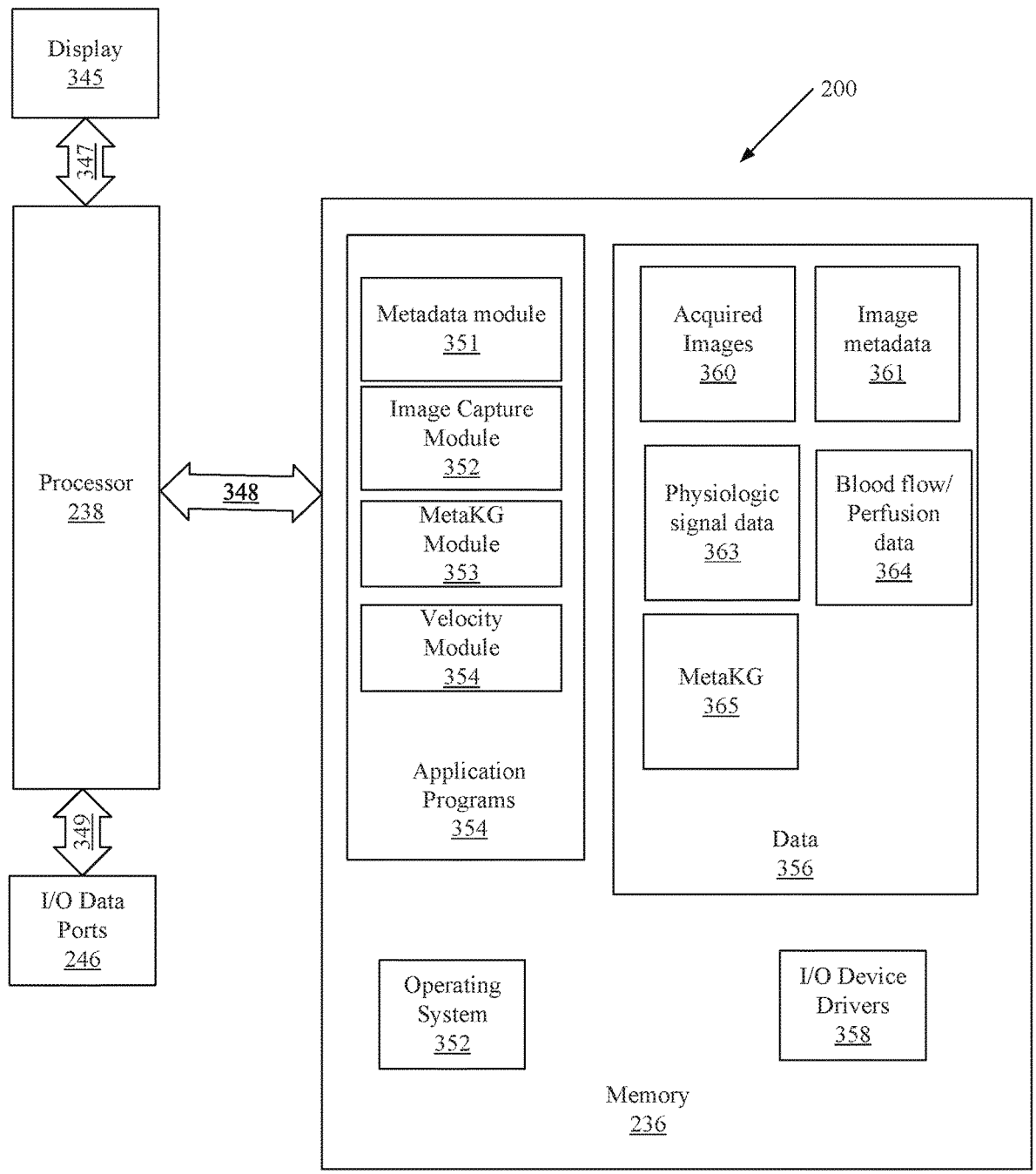
FIG. 20 is a more detailed block diagram of the data processing system illustrated in FIG. 19 in accordance with some embodiments of the present inventive concept(s).

Referring now to FIGS. 19 and 20, a data processing system 200 that may be used in the system 100 illustrated in FIG. 1 in accordance with some embodiments of the inventive concept will be discussed. The data processing system 200 may be included in the metaKG device 112, the camera 130 or split between various elements of the system 100 without departing from the scope of the present inventive concept. As illustrated in FIG. 19, an exemplary embodiment of a data processing system 200 suitable for use in the system 100 of FIG. 1 includes a user interface 244 such as a keyboard, keypad, touchpad or the like, I/O data ports 246 and a memory 236 that communicates with a processor 238. The I/O data ports 246 can be used to transfer information between the data processing system 200 and another computer system or a network. These components may be conventional components, such as those used in many conventional data processing systems, which may be configured to operate as described herein.

Referring now to FIG. 20, a more detailed block diagram of the data processing system 200 in accordance with some embodiments of the present inventive concept will be discussed. The processor 238 communicates with a display 345 via and address/data bus 347, the memory 236 via an address/data bus 348 and the I/O data ports 246 via an address/date bus 349. The processor 238 can be any commercially available or custom microprocessor or ASICs. The memory 236 is representative of the overall hierarchy of memory devices containing the software and data used to implement the functionality of the data processing system 200. The memory 236 can include, but is not limited to, the following types of devices: cache, ROM, PROM, EPROM, EEPROM, flash memory, SRAM, and DRAM.

As shown in FIG. 20, the memory 236 may include several categories of software and data used in the data processing system 200: an operating system 352; application programs 354; input/output (I/O) device drivers 358; and data 356. As will be appreciated by those of skill in the art, the operating system 352 may be any operating system suitable for use with a data processing system, such as Mac OSX, OS/2, AIX or zOS from International Business Machines Corporation, Armonk, N.Y., Windows95, Windows98, Windows2000, WindowsXP, Windows 8, Windows 10 or Vista from Microsoft Corporation, Redmond, Wash., Unix, Linux, LabView, or a real-time operating system such as QNX or VxWorks, or the like. The I/O device drivers 358 typically include software routines accessed through the operating system 352 by the application programs 354 to communicate with devices such as the I/O data port(s) 246 and certain memory 236 components. The application programs 354 are illustrative of the programs that implement the various features of the data processing system 200 included a system in accordance with some embodiments of the present inventive concept and preferably include at least one application that supports operations according to some embodiments of the present inventive concept. Finally, the data 356 represents the static and dynamic data used by the application programs 354, the operating system 352, the I/O device drivers 358, and other software programs that may reside in the memory 236.

As illustrated in FIG. 20, the data 356 according to some embodiments of the present inventive concept may include acquired images 360, image metadata 361, physiologic signal data 363, calculated blood flow/perfusion rates (velocity data) 364 and MetaKG data 365. Although the data 356 illustrated in FIG. 20 includes five different files 360, 361, 363, 364 and 365 embodiments of the present inventive concept are not limited to this configuration. Two or more files may be combined to make a single file; a single file may be split into two or more files and the like without departing from the scope of the present inventive concept.

As further illustrated in FIG. 20, the application programs 354 may include a metadata module 351, an image capture module 352, a MetaKG module 353 and velocity module 354 in accordance with some embodiments of the inventive concept. While the present inventive concept is illustrated, for example, with reference to the metadata module 351, the image capture module 352, the MetaKG module 353 and the velocity module 354 being application programs in FIG. 20, as will be appreciated by those of skill in the art, other configurations may also be utilized while still benefiting from the teachings of the present inventive concept. For example, the metadata module 351, the image capture module 352, the MetaKG module 353 and the velocity module 354 may also be incorporated into the operating system 352 or other such logical division of the data processing system 300. Thus, the present inventive concept should not be construed as limited to the configuration of FIG. 20, but is intended to encompass any configuration capable of carrying out the operations described herein.

Furthermore, while the metadata module 351, the image capture module 352, the MetaKG module 353 and the velocity module 354 are illustrated in a single data processing system, as will be appreciated by those of skill in the art, such functionality may be distributed across one or more data processing systems. Thus, the present inventive concept should not be construed as limited to the configuration illustrated in FIGS. 19 and 20, but may be provided by other arrangements and/or divisions of function between data processing systems.

As discussed above with respect to FIG. 1, at least one source 120 may illuminate a sample of tissue/organ and light may be reflected into a camera. The camera 130/image capture module 352 may receive the reflected light and provide it to the imaging processing device 110 to provide an image 360. These images may be processed (metadata module 351) to provide metadata 361 associated therewith and an MetaKG signal 365 (surrogate EKG signal) may be determined by the MetaKG module 353 using the Physiologic signal data 363 and the metadata 361 as discussed above. As also discussed above, this surrogate EKG signal (MetaKG signal) may be used to provide blood flow and perfusion data 364 by the velocity module 354. In particular, the data 356 may be used by the metaKG module 353 to provide blood flow and perfusion data synchronized with a surrogate EKG signal (metaKG signal).

Figure 21:
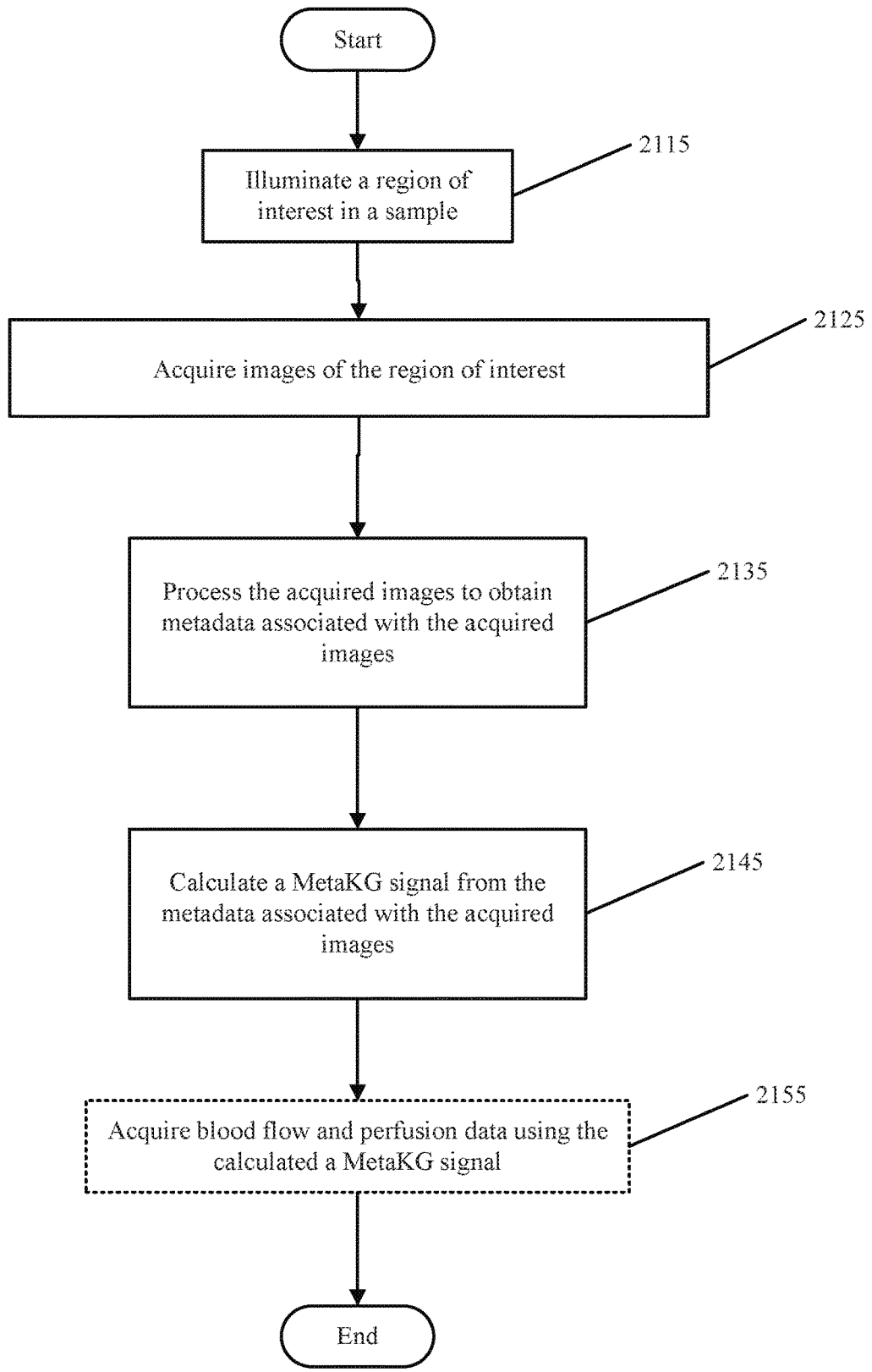
FIGS. 21 through 23 are flowcharts illustrating operations for combining images in accordance with various embodiments of the present inventive concept(s).

Operations in accordance with various embodiments of the inventive concept will now be discussed with respect to the flowcharts of FIGS. 21 through 23. Operations for calculating a MetaKG signal begin at block 2115 by illuminating a region of interest in a sample with at least one light source, for example, a near-infrared (NIR) light source and/or a visible light source. Images of the region of interest are acquired (2125). The acquired images are processed to obtain metadata associated with the acquired images (block 2135). The MetaKG signal is calculated from the metadata associated with the acquired images (block 2145). In some embodiments, the MetaKG signal may be calculated or derived from one of raw (reflectance images) images and perfusion (analyzed) images (processed images). In some embodiments, the sample may be one of tissue and an organ.

In some embodiments, blood flow and perfusion data may be acquired using the calculated MetaKG signal (block 2155). Dotted lines indicating optional subject matter.

Figure 22:
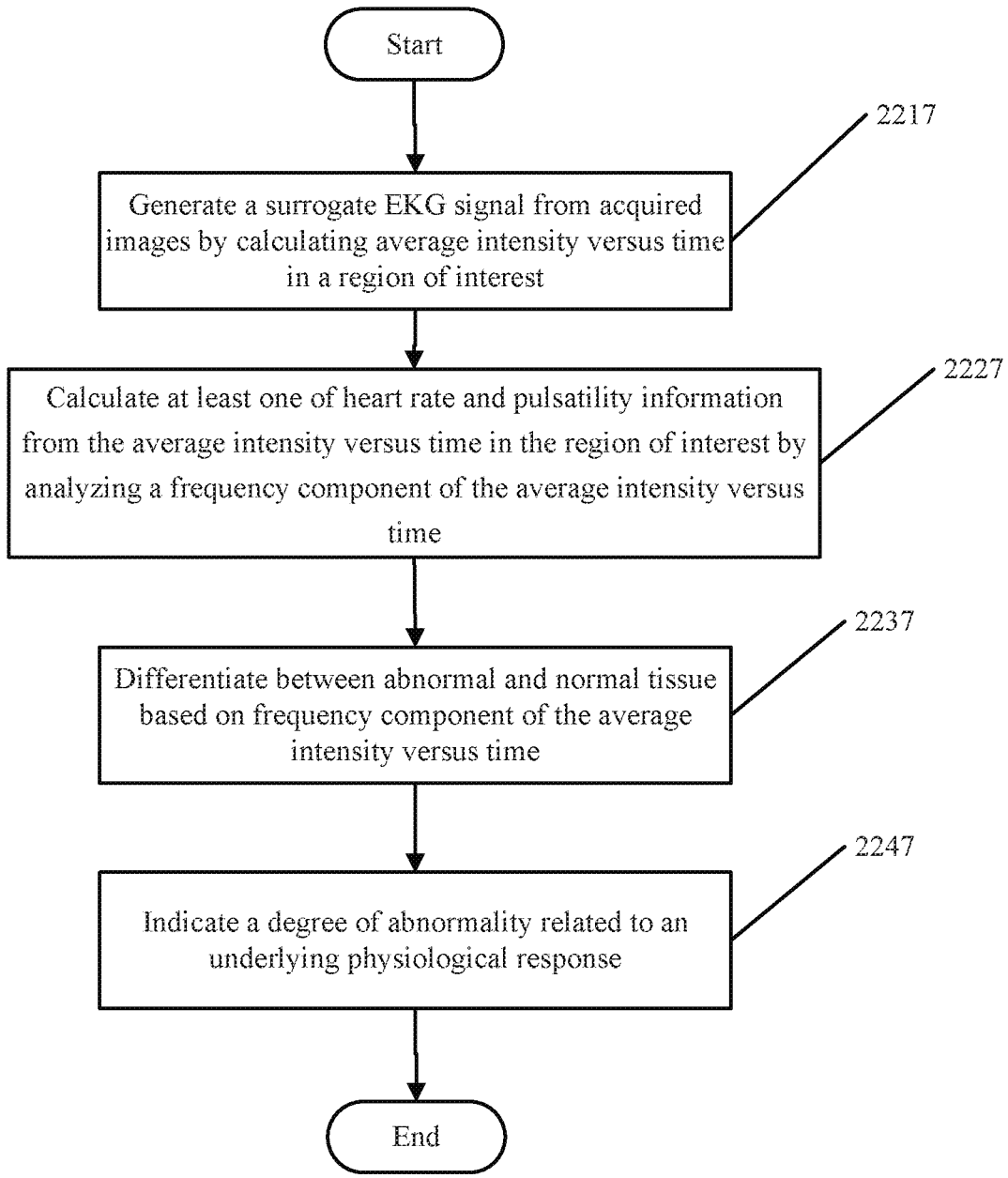

Referring now to FIG. 22, operations begin at block 2217 by generating the MetaKG signal from acquired images by calculating average intensity versus time in the region of interest. At least one of heart rate and pulsatility information may be calculated from the average intensity versus time in the region of interest by analyzing a frequency component of the average intensity versus time (block 2227). In some embodiments, heart rate variability (HRV) may be extracted from the heart rate calculated from the average intensity versus time in the region of interest. As used herein, the term "heart rate variability" refers to a measure of changes of the heart rate over time. This change may be large or small, and over a small or large time-interval. Normally, the heart rate is not absolutely regular, and one can quantify the degree of changes of the heart rate over a certain period of time, for example, the heart beats faster and slower with respiration. Some types of HRV are indicative of abnormal physiological status, and/or diseases.

Abnormal and normal tissue may be differentiated based on a frequency component of the average intensity versus time (block 2237). A degree of abnormality related to an underlying physiological response may be indicated (block 2247).

Figure 23:
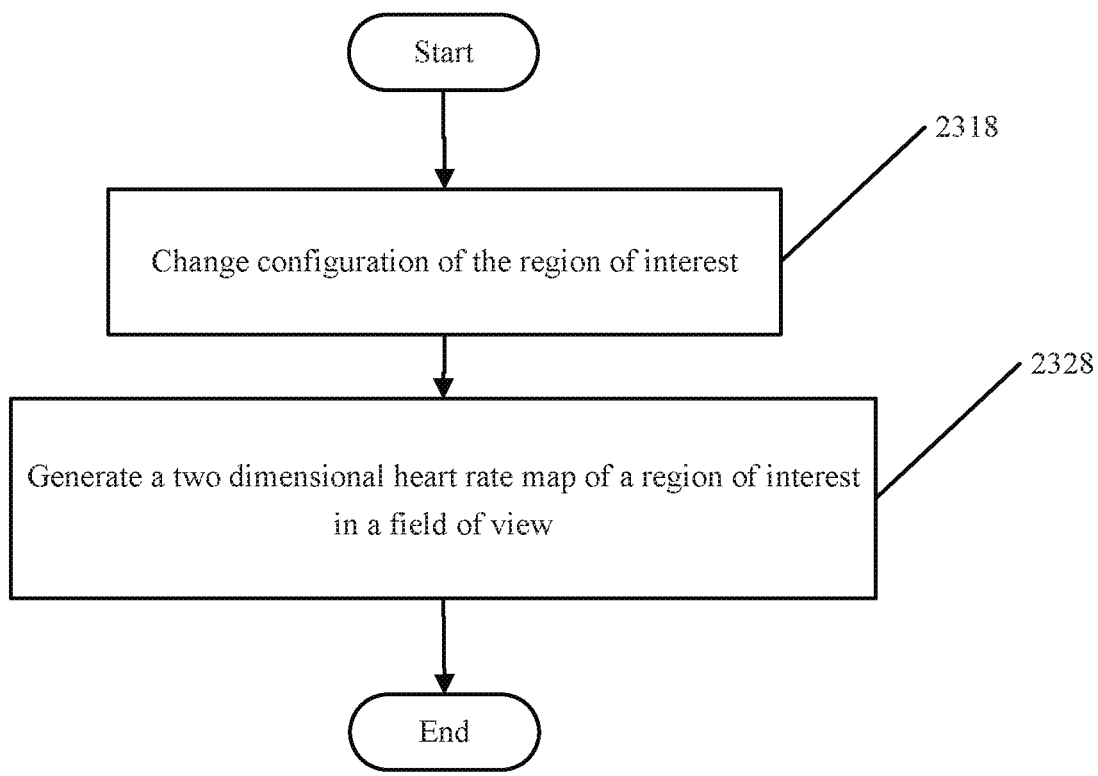

Referring now to FIG. 23, a configuration of the region of interest may be changed (block 2318). For example, one of the size and the location of the region of interest may be changed. A two dimensional heart rate map may be generated of a region of interest in a field of view (block 2328).

As discussed above, in some embodiments of the present inventive concept, a surrogate EKG (MetaKG) may be calculated using average intensity of the raw images. However, in some embodiments, the MetaKG may be calculated using average intensity of speckle contrast images as will be discussed further below with respect to FIGS. 24A through 29. Embodiments of the present inventive concept illustrated in FIGS. 24A through 29 discuss processing the images in the time domain, frequency domain and the time-frequency domain as discussed below. Thus, FIGS. 2A-3B, 5, 7, 8D, 9C, 10C, 11B, 12B, 12D, 13B, 14B, 14D, 15B, 16B, 16D, 17B, 18B and 18D illustrate MetaKG signals calculated from a raw image (reflectance image) in accordance with some embodiments of the present inventive concept. FIGS. 25, 26 (frequency domain), 27 (time-frequency domain), 28A, 28B (frequency domain) and FIG. 29 (time-frequency domain) illustrate MetaKG calculated from perfusion images (LSI, LDI etc.) in accordance with some embodiments of the present inventive concept.

Figure 24B:
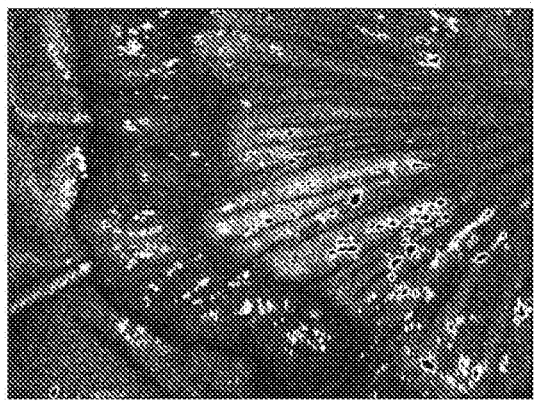
FIGS. 24A through 24D illustrate laser speckle imaging of a pig intestine in accordance with some embodiments of the present inventive concept.
Figure 24D:
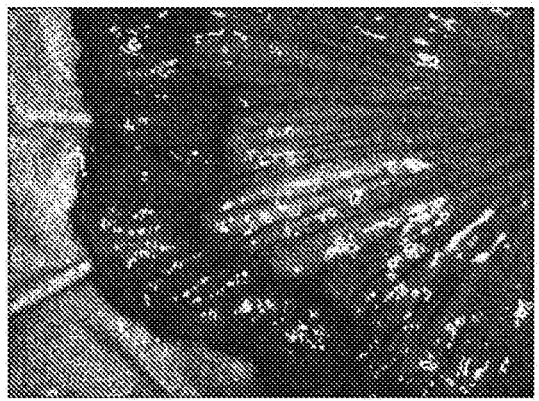
Figure 24A:
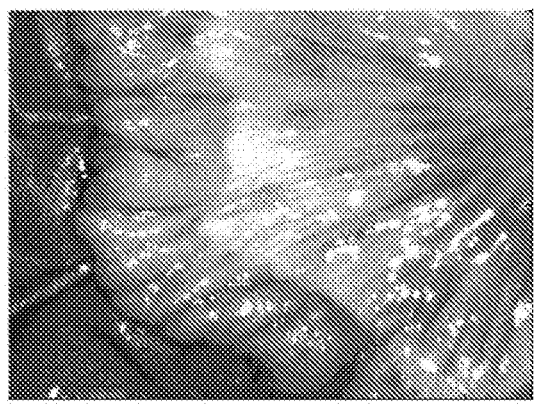
Figure 24C:
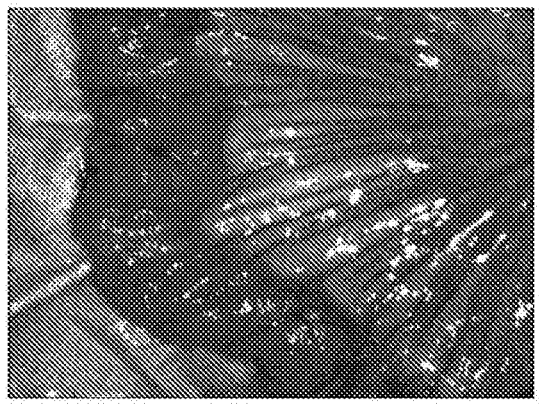

Referring first to FIGS. 24A and 24B, laser speckle imaging examples of a pig intestine will be discussed. FIGS. 24A and 24B illustrate a raw NIR laser speckle image and a NIR laser speckle contrast image, respectively. FIGS. 24C and 24D illustrate a raw VL laser speckle image and a VL laser speckle contrast image, respectively. As illustrated, the difference between the raw laser speckle images (24A and 24D) and the laser speckle contrast images (24B and 24D) is more apparent in the NIR images (24A and 24B) than it is in the VL images (24C and 24D). This is indicative of the fact the NIR laser speckle contrast image (24B) provides better insights into blood flow and perfusion than the raw NIR laser speckle image (24A).

Referring now to FIGS. 25A and 25B, graphs illustrating time-domain (or spectral) analysis of MetaKG signals will be discussed. FIG. 25A illustrates an NIR-MetaKG (X) versus time and FIG. 25B illustrates a VL-MetaKG (Y) versus time. The X lines on both plots represent the large amplitude slow trend of the MetaKG caused by the respiratory activity related movement. Both NIR-MetaKG (W) and VL-MetaKG (Y) are contaminated by this noise to the same degree.

Referring now to FIGS. 26A and 26B, graphs illustrating frequency-domain (or spectral) analysis of MetaKG signals will be discussed. FIG. 26A illustrates the Power Spectral Density (PSD) of NIR-MetaKG versus frequency and FIG. 26B illustrates the PSD of VL-MetaKG versus frequency, both graphs illustrating respiratory activity and cardiac activity in the frequency domain. Thus, PSD is a measure of strength of a given signal's specific frequency components.

Referring now to FIGS. 27A and 27B, graphs illustrated frequency-time domain (or spectrogram) analysis of MetaKG signals will be discussed. FIG. 27A illustrates a spectrogram of NIR-MetaKG and FIG. 27B illustrates a spectrogram of VL-MetaKG, both including cardiac and respiratory activity. The spectrogram of MetaKG signals reveals the frequency-domain spectral contents of the signals over time. Both MetaKG signals are severely contaminated by the respiratory activity related noise. The spectrogram of the NIR-MetaKG (27A) shows a slight sign of cardiac activity (labeled line), which is much weaker than the respiratory activity related noise.

Figure 28A:
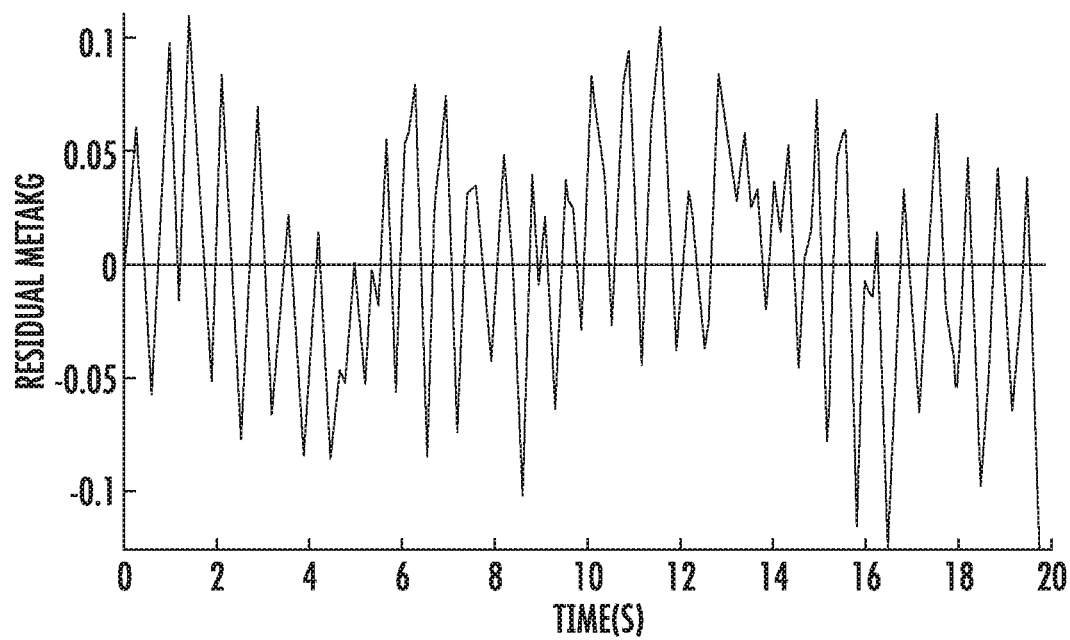
FIGS. 28A and 28B are graphs illustrating residual MetaKG versus time/frequency in accordance with some embodiments of the present inventive concept.
Figure 28B:
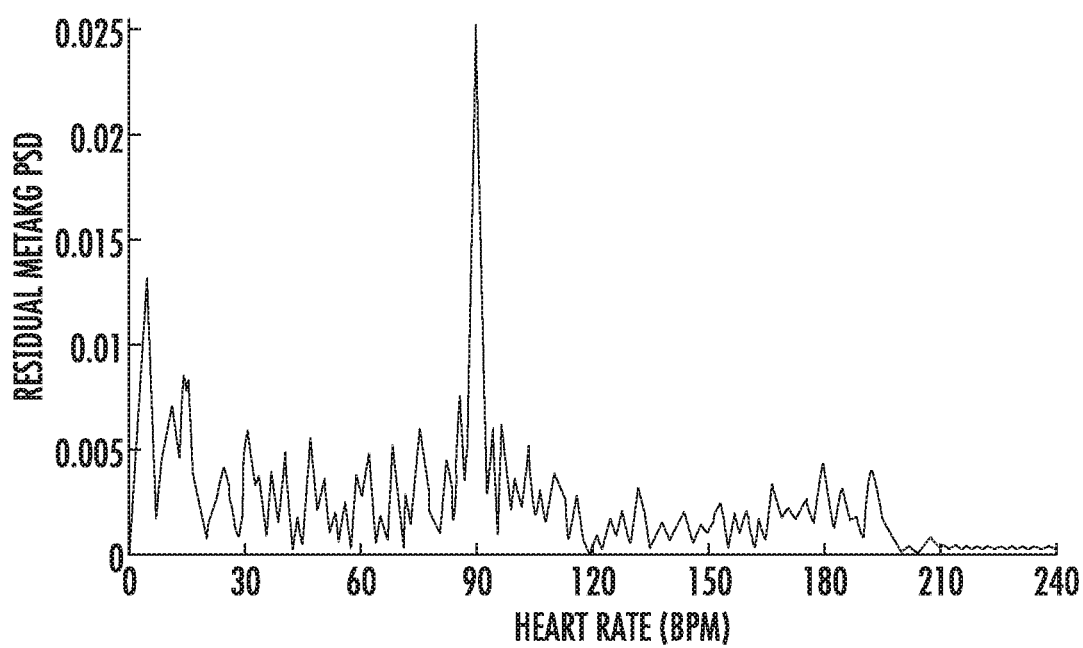

Referring now to FIGS. 28A and 28B, graphs illustrating residual MetaKG will be discussed. FIG. 28A illustrates residual-MetaKG versus time and FIG. 28B illustrates residual-MetaKG versus frequency. By utilizing both NIR-MetaKG and VL-MetaKG, the residual-MetaKG can be extracted. The PSD of the residual-MetaKG (FIG. 28B) clearly shows that the signal's dominant component is related to the cardiac activity (about 90 bpm), not the respiratory activity.

Figure 29:
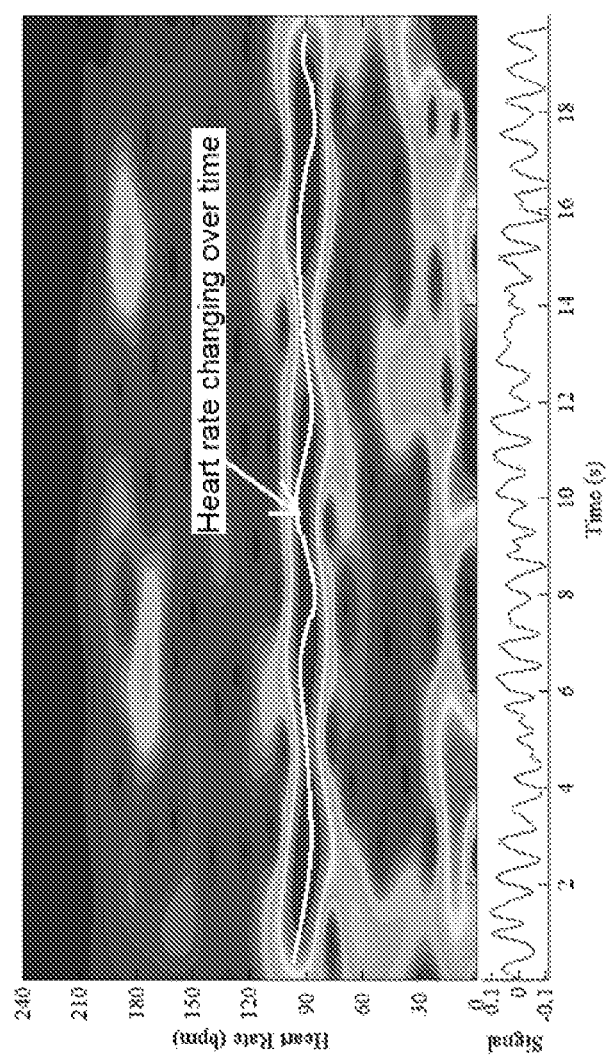
FIG. 29 is a graph illustrating frequency-time domain (or spectrogram) analysis of residual-MetaKG signals in accordance with some embodiments of the present inventive concept.

Referring now to FIG. 29, a graph illustrating frequency-time domain (or spectrogram) analysis of the residual-MetaKG will be discussed. The spectrogram of the residual-MetaKG signal illustrates in FIG. 29 reveals that the signal is free from the respiratory activity related noise. The instantaneous heart rate changing over time is marked thereon. By utilizing the residual-MetaKG, the slight changes in the heart rate over time can be tracked and heart rate variability (HRV—defined above) can be computed.

Given the residual MetaKG, there are many ways to calculate HRV. However, most of them are designed to calculate HRV over a long period of time, for example, at least 5 minutes. MetaKG in accordance with embodiments discussed herein tends to be shorter than average (20 s~1 min), the difference between the maximum and minimum HR values may be obtained and may be used as a HRV index. An extended Kalman filter may be used to estimate the heart rate series of any given Meta-KG. Then, the HRV may be determined as the difference between the maximum and minimum heart rate values.

Figure 30:
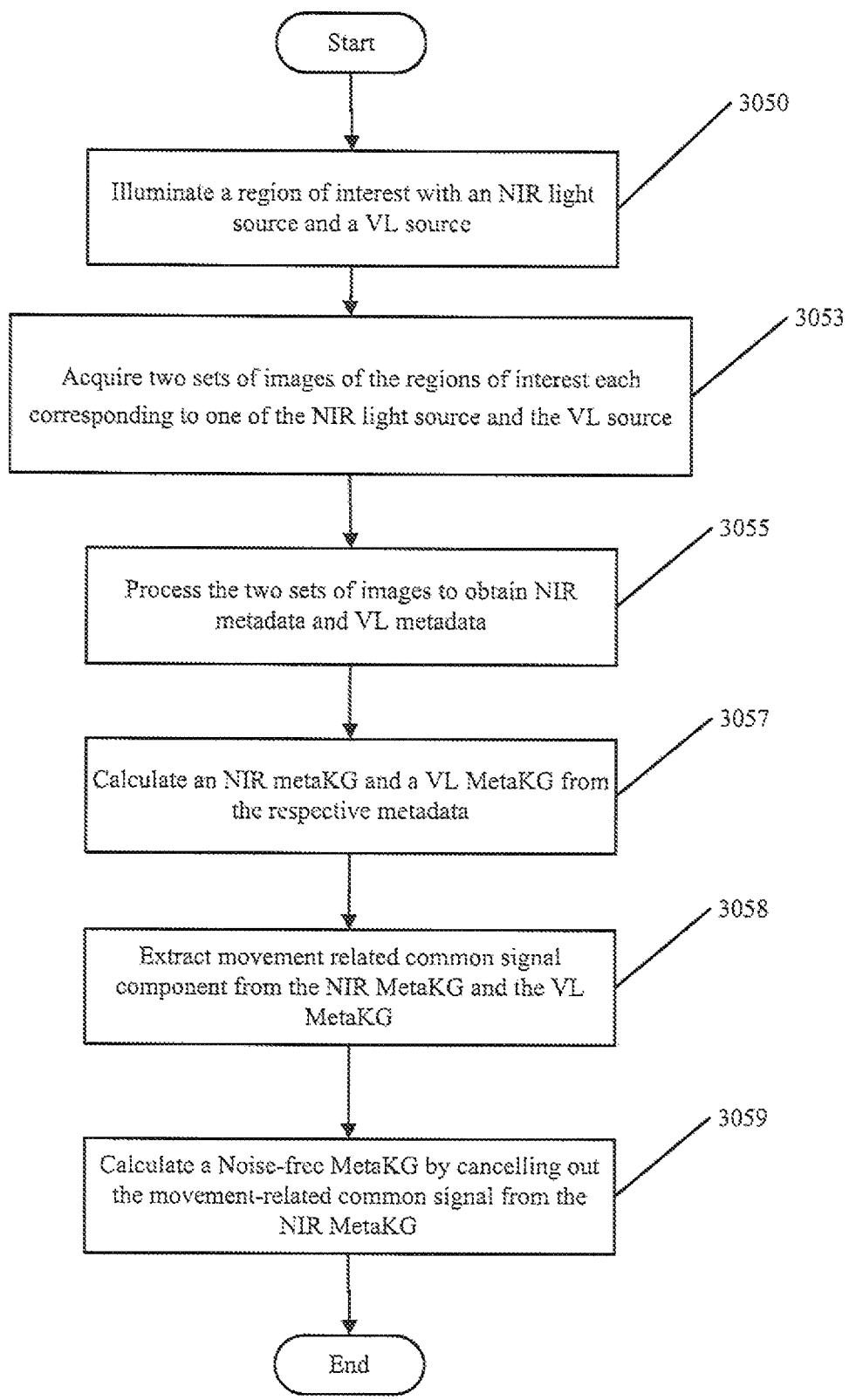
FIG. 30 is a flow chart illustrating operations according to some embodiments of the present inventive concept.

Referring now to FIG. 30, operations for a two wavelength embodiment in accordance with some embodiments will be discussed. As illustrated in FIG. 30, operations for removing movement-related artifacts from a MetaKG signal using dual wavelength light sources begins at block 3050 by illuminating a region of interest in a sample with a near-infrared (NIR) light source and a visible light (VL) source. Two sets of images of the region of interest are acquired, each corresponding to one of the NIR light source and the VL source (block 3053). The two sets of images are processed to obtain NIR-metadata and VL-metadata (block 3055). An NIR MetaKG and a VL MetaKG are calculated from the NIR-metadata and the VL metadata, respectively (block 3057). A movement-related common signal component is extracted from the NIR MetaKG and the VL MetaKG (block 3058). A noise-free MetaKG is calculated by cancelling out the movement-related common signal component from the NIR MetaKG (block 3059).

As discussed above, embodiments of the present inventive concept that use multiple wavelengths to acquire multispectral images can remove noise due to motion artifacts caused by, for example, respiratory activity (FIGS. 26-29). Single wavelength technologies may not be able to effectively remove such noise artifacts.

Referring now to FIGS. 31A through 31G, a block diagram illustrating Hemodynamic Status Parameters (HSP) that may be derived from MetaKG in accordance with embodiments discussed herein will be discussed. As illustrated in FIG. 31, the HSPs may include Heart Rate (HR), heart rate variability (HRV), R-to-R interval (RRI), and RRI Standard Deviation (RRISD) as illustrated in FIG. 31C, systolic Blood Pressure threshold (SBt) as illustrated in FIG. 31G, and ratexpressure product (RPP), instantaneous perfusion in systole and diastole, frequency analysis and time-frequency analysis of the perfusion curve, and contractility index (slope of the perfusion curve) as illustrated in FIGS. 31A-31B and 31D-31F. In some embodiments, the MetaKG may be used to derive additional HSPs such as tissue oxygen content, hemoglobin content, temperature, and the like. The opportunity to capture these relevant hemodynamic parameters non-invasively from imaging is an innovation for clinical point-of-care monitoring technologies. Real-time integration with physiologic blood flow and perfusion data will further augment the accuracy and potential diagnostic and therapeutic impact of these digital HSP data trended over time.

It will be understood that embodiments of the present inventive concept may be used in any format of clinical imaging, which includes both surgical imaging (usually an in-patient application) and other out-patient imaging procedure (non-surgical application) without departing from the scope of the present inventive concept.

Example embodiments are described above with reference to block diagrams and/or flowchart illustrations of methods, devices, systems and/or computer program products. It is understood that a block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means (functionality) and/or structure for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the functions/acts specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, example embodiments may be implemented in hardware and/or in software (including firmware, resident software, micro-code, etc.). Furthermore, example embodiments may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Computer program code for carrying out operations of data processing systems discussed herein may be written in a high-level programming language, such as Java, AJAX (Asynchronous JavaScript), C, and/or C++, for development convenience. In addition, computer program code for carrying out operations of example embodiments may also be written in other programming languages, such as, but not limited to, interpreted languages. Some modules or routines may be written in assembly language or even micro-code to enhance performance and/or memory usage. However, embodiments are not limited to a particular programming language. It will be further appreciated that the functionality of any or all of the program modules may also be implemented using discrete hardware components, one or more application specific integrated circuits (ASICs), or a field programmable gate array (FPGA), or a programmed digital signal processor, a programmed logic controller (PLC), or microcontroller.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated.

In the drawings and specification, there have been disclosed example embodiments of the inventive concept. Although specific terms are employed, they are used in a generic and descriptive sense only and not for purposes of limitation, the scope of the inventive concept being defined by the following claims.

That which is claimed:

1. A method for calculating a MetaKG signal, the method comprising:
   illuminating a region of interest in a sample with at least one multi-wavelength light source, wherein the multi-wavelength light source is a near-infrared (NIR) light source and/or a visible light source;
   acquiring multi-spectral images of the region of interest using a multi-wavelength camera;
   processing the acquired multi-spectral images to obtain metadata associated with the acquired multi-spectral, images; and
   calculating the MetaKG signal from the metadata associated with the acquired multi-spectral images,
   wherein calculating the MetaKG signal comprises:
   calculating the MetaKG signal using average intensity of speckle contrast images derived from the acquired multi-spectral images to provide an average intensity MetaKG signal;
   calculating a frequency MetaKG signal using frequency analysis;
   calculating a time-frequency MetaKG signal using time-frequency analysis; and/or
   calculating a multi-spectral MetaKG signal using multi-spectral signal processing to remove motion artifacts and improve signal quality;
   wherein calculating the time-frequency MetaKG comprises:
      separating the MetaKG signal into a cardiac related signal and a respiratory related signal to provide a cardiac MetaKG and a respiratory MetaKG;
      determining a specific frequency range for two-dimensional frequency time signals using a power spectral density analysis of the MetaKG signal; and
      reconstructing each MetaKG by averaging the determined specific frequency range of the two-dimensional frequency-time signals; and
   wherein at least one of illuminating, acquiring, processing and calculating is performed by at least one processor.

2. The method of claim 1, further comprising one of:
   deriving the average intensity MetaKG signal, the frequency MetaKG signal, the time-frequency MetaKG signal and/or the multi-spectral MetaKG signal from raw multi-spectral images; or
   deriving the average intensity MetaKG signal, the frequency MetaKG signal, the time-frequency MetaKG signal and/or the multi-spectral MetaKG signal from multi-spectral perfusion images.

3. The method of claim 1, further comprising acquiring blood flow and perfusion data using one or more of the calculated average intensity MetaKG signal, the frequency MetaKG signal, the time-frequency MetaKG signal and/or the multi-spectral MetaKG signal.

4. The method of claim 3, wherein the average intensity of the speckle contrast images is average contrast intensity versus time from the speckle contrast images in the region of interest.

5. The method of claim 4, further comprising calculating at least one of heart rate and pulsatility information from the average contrast intensity versus time in the region of interest by analyzing a frequency component of the average contrast intensity versus time.

6. The method of claim 5, further comprising:
   differentiating between abnormal and normal tissue based on the frequency component of the average contrast intensity versus time; and
   indicating a degree of abnormality related to an underlying physiological response.

7. The method of claim 5, further comprising extracting heart rate variability (HRV) information from the heart rate calculated from the average contrast intensity versus time in the region of interest.

8. The method of claim 1, further comprising:
   changing configuration of the region of interest; and
   generating a two dimensional heart rate map of the region of interest in a field of view.

9. The method of claim 8, wherein changing the configuration of the region of interest comprises changing at least one of a size or a location of the region of interest.

10. The method of claim 1, wherein the sample comprises one of tissue or an organ.

11. The method of claim 3, further comprising determining at least one physiologic status parameter including Heart Rate (HR); heart rate variability (HRV); R-to-R interval (RRI); RRI Standard Deviation (RRISD); systolic Blood Pressure threshold (SBt); diastolic blood pressure threshold (DBt); rate×pressure product (RPP); instantaneous perfusion in systole and diastole; frequency analysis and time-frequency analysis of a perfusion curve; and contractility index including slope of the perfusion curve based on the calculated average intensity MetaKG signal, the frequency MetaKG signal, the time-frequency MetaKG signal and/or the multi-spectral MetaKG signal.

12. The method of claim 1, further comprising determining at least one physiologic status parameter including at least one of tissue oxygen content, hemoglobin content, and temperature based on the calculated average intensity Met KG signal, the frequency MetaKG signal, the time-frequency MetaKG signal and/or the multi-spectral MetaKG.

13. A computer system for calculating a MetaKG signal, the system comprising:
   a processor; and
   a memory coupled to the processor and comprising computer readable program code that when executed by the processor causes the processor to:
   direct at least one multi-wavelength light source to illuminate a region of, interest in a sample, wherein the at least one multi-wavelength light source is a near-infrared (NIR) light source and/or a visible light source;
   process acquired multi-spectral images of the region of interest to obtain metadata associated with the acquired multi-spectral images, the multi-spectral images being acquired with a multi-wavelength camera; and calculate the MetaKG signal from the metadata associated with the multi-spectral images, wherein the computer readable program code that causes the processor to calculate the MetaKG signal further comprises computer readable program code that when executed by the processor causes the processor to:

calculate the MetaKG signal using average intensity of speckle contrast images derived from the acquired multi-spectral images to provide an average intensity MetaKG signal;

calculate a frequency MetaKG signal using frequency analysis;

calculate a time-frequency MetaKG signal using time-frequency analysis; and/or calculate a multi-spectral MetaKG signal using multi-spectral signal processing to remove motion artifacts and improve signal quality, wherein the computer system further comprises computer readable program code to calculate the time-frequency MetaKG by causing the processor to:

separate the MetaKG signal into a cardiac related signal and a respiratory related signal to provide a cardiac MetaKG and a respiratory MetaKG;

determine a specific frequency range for two-dimensional frequency time signals using a power spectral density analysis of the MetaKG signal; and reconstruct each MetaKG by averaging the determined specific frequency range of the two-dimensional frequency-time signals.

14. The system of claim 13, wherein the processor further performs operations comprising acquiring blood flow and perfusion data using the calculated average intensity MetaKG signal, the frequency MetaKG signal, the time-frequency MetaKG signal and/or the multi-spectral MetaKG signal.

15. The system of claim 14, wherein the average intensity of the speckle contrast images is average contrast intensity versus time in the region of interest.

16. The system of claim 15, wherein the processor further performs operations comprising calculating at least one of heart rate and pulsatility information from the average intensity versus time in the region of interest by analyzing a frequency component of the average intensity versus time.

17. The system of claim 16, wherein the processor further performs operations comprising:

differentiating between abnormal and normal tissue based on the frequency component of the average intensity versus time; and indicating a degree of abnormality related to an underlying physiological response.

18. The system of claim 16, wherein the processor is further configured to extract heart rate variability (HRV) information from the heart rate calculated from the average intensity versus time in the region of interest.

19. The system of claim 13, wherein the processor further performs operations comprising:

changing configuration of the region of interest; and generating a two dimensional heart rate map of the region of interest in a field of view.

20. The system of claim 19, wherein the processor further performs operations comprising directing the multi-wavelength camera to change at least one of a size or avocation of the region of interest.

21. A computer program product for calculating a MetaKG signal, the computer program product comprising:

a non-transitory computer readable storage medium having computer readable program code embodied in the medium, the computer readable program code comprising:

computer readable program code to direct at least one multi-wavelength light source to illuminate a region of interest in a sample, wherein the multi-wavelength light source is a near-infrared (NIR) light source and/or a visible light source;

computer readable program code to process multi-spectral images of the region of interest obtained using a multi-wavelength camera to obtain metadata associated with the multi-spectral images; and computer readable program code to calculate the MetaKG signal from the metadata associated with the multi-spectral images, wherein the computer readable program code to calculate the MetaKG signal comprises:

computer readable program code to calculate the MetaKG signal using average intensity of speckle contrast images derived from the acquired multi-spectral images to provide an average intensity MetaKG signal;

computer readable program code to calculate a frequency MetaKG signal using frequency analysis;

computer readable program code to calculate a time-frequency MetaKG signal using time-frequency analysis; and/or computer readable program code to calculate a multi-spectral MetaKG signal using multi-spectral signal processing to remove motion artifacts and improve signal quality, wherein the computer readable program code to calculate the time-frequency MetaKG comprises:

computer readable program code to separate the MetaKG signal into a cardiac, related signal and a respiratory related signal to provide a cardiac MetaKG and a respiratory MetaKG;

computer readable program code to determine a specific frequency range for two-dimensional frequency time signals using a power spectral density analysis of the MetaKG signal; and computer readable program code to reconstruct each MetaKG by averaging the determined specific frequency range of the two-dimensional frequency-time signals.

22. The computer program product of claim 21, further comprising computer readable program code to acquire blood flow and perfusion data using the calculated average intensity MetaKG signal, the frequency MetaKG signal, the time-frequency MetaKG signal and/or the multi-spectral MetaKG signal.

23. The computer program product of claim 22, wherein the computer readable program code to calculate the average intensity MetaKG signal calculates the average intensity as average intensity versus time in the region of interest.

24. The computer program product of claim 23, further comprising computer readable program code to calculate at least one of heart rate and pulsatility information from the average intensity versus time in the region of interest by analyzing a frequency component of the average intensity versus time.

25. The computer program product of claim 24, further comprising:

computer readable program code to differentiate between abnormal and normal tissue based on the frequency component of the average intensity versus time; and computer readable program code to indicate a degree of abnormality related to an underlying physiological response.

26. The computer program product of claim 24, further comprising computer readable program code to extract heart rate variability (HRV) information from the heart rate calculated from the average intensity versus time in the region of interest.

27. The computer program product of claim 21, further comprising:
computer readable program code to direct the multi-wavelength camera to change configuration of the region of interest; and
computer readable program code to generate a two dimensional heart rate map of a region of interest in a field of view.

28. The computer program product of claim 27, wherein the computer readable program code to change the configuration of the region, of interest comprises computer readable program code to direct the camera to change at least one of a size or a location of the region of interest.

29. The method of claim 1, wherein a frequency specific MetaKG(MetaKG$_{F1-F2}$(t)) is calculated as:

$$MetaKG_{F1-F2}(t) = \frac{\sum_{f=F1}^{F2} a \times TF(f, t) + b}{F2 - F1}$$

wherein TF(f,t) is a frequency-time transform of the average intensity versus time signal; F1 and F2 are lower and upper limits of a specific frequency range, respectively; and a and b are parameters for normalization.

30. A method for calculating a MetaKG signal, the method comprising:
illuminating a region of interest in, a sample with at least one multi-wavelength light source, wherein the multi-wavelength light source is a near-infrared (NIR) light source and/or a visible light source;
acquiring multi-spectral images of the region of interest using a multi-wavelength camera;
processing the acquired multi-spectral images to obtain metadata associated with the acquired multi-spectral images; and
calculating the MetaKG signal from the metadata associated with the acquired multi-spectral images,
wherein calculating the MetaKG signal comprises:
calculating the MetaKG signal using average intensity of speckle contrast images derived from the acquired multi-spectral images to provide an average intensity MetaKG signal;
calculating a frequency MetaKG signal using frequency analysis;
calculating a time-frequency MetaKG signal using time-frequency analysis; and/or calculating a multi-spectral MetaKG signal using multi-spectral signal processing to remove motion artifacts and improve signal quality,
wherein calculating a multi-spectral MetaKG signal comprises:
calculating a residual MetaKG(Meta$_{KG\lambda1,\lambda2}$(t)) as:

$$MetaKG_{\lambda1,\lambda2}(t) = \frac{\sum_{y=1}^{M} \sum_{x=1}^{N} a \times Img_{\lambda1}(x, y, t) - b \times Img_{\lambda2}(x, y, t) + e}{M \times N};$$

or $$MetaKG_{\lambda1,\lambda2}(t) = \frac{\sum_{y=1}^{M} \sum_{x=1}^{N} a \times \frac{Img_{\lambda1}(x, y, t)}{Img_{\lambda2}(x, y, t)} + b}{M \times N}$$

wherein Img$_{\lambda,1}$(x,y,t) is raw or speckle contrast images of a first wavelength; Img$_{\lambda,2}$(x,y,t) is raw or speckle contrast images of a second wavelength; a, b and c are parameters for normalization; and M and N are a number of pixels along x and y axes, respectively.

31. The method of claim 30, wherein the multi-spectral MetaKG is used to determine physiologic, status parameters (PSPs) by determining specific quantitative aspects of the multi-spectral MetaKG that represent one or more PSPs.

32. The method of claim 31, wherein the PSPs comprise Heart Rate (HR); heart rate variability (HR V); R-to-R interval (RRI); RRI Standard Deviation (RRISD); systolic Blood Pressure threshold (SBt); diastolic blood pressure threshold (DBt); rate×pressure product (RPP); instantaneous perfusion in systole and diastole; frequency analysis and time-frequency analysis of a perfusion curve; and/or contractility index including slope of the perfusion curve based on the calculated MetaKG signal.

33. The method of claim 32, wherein the multispectral MetaKG generates a specific value that represents a relative perfusion quantification for a pixel at a single point in time, wherein differences at the single point in time between MetaKG values can differentiate thresholds for PSPs, the method further comprising observing a change in the MetaKG for the pixel to provide a different representation of physiology status.

* * * * *

UNITED STATES PATENT AND TRADEMARK OFFICE
CERTIFICATE OF CORRECTION

PATENT NO. : 10,792,492 B2  
APPLICATION NO. : 15/518545  
DATED : October 6, 2020  
INVENTOR(S) : Cheng Chen et al.

Page 1 of 1

It is certified that error appears in the above-identified patent and that said Letters Patent is hereby corrected as shown below:

In the Claims

Column 22, Line 36, change "claim 3" to -- claim 1 --.

Column 22, Line 51, change "Met" to -- Meta --.

Column 22, Line 60, change "region of, interest" to -- region of interest --.

Column 23, Line 64, change "avocation" to -- a location --.

Column 24, Line 36, change "cardiac, related" to -- cardiac related --.

Column 25, Line 18, change "region of, interest" to -- region of interest --.

Column 25, Line 36, change "interest in, a sample" to -- interest in a sample --.

Signed and Sealed this  
First Day of December, 2020

Andrei Iancu  
*Director of the United States Patent and Trademark Office*